United States Patent
Sayegh et al.

(10) Patent No.: US 6,280,957 B1
(45) Date of Patent: Aug. 28, 2001

(54) COSTIMULATORY BLOCKADE AND MIXED CHIMERISM IN ALLO-TRANSPLANTATION

(75) Inventors: Mohamed Sayegh, Westwood; Megan Sykes, Charlestown, both of MA (US)

(73) Assignee: The General Hospital Corporation, Charlestown, MA (US)

( * ) Notice: Subject to any disclaimer, the term of this patent is extended or adjusted under 35 U.S.C. 154(b) by 0 days.

(21) Appl. No.: 09/245,614

(22) Filed: Feb. 4, 1999

Related U.S. Application Data

(60) Provisional application No. 60/073,864, filed on Feb. 4, 1998.

(51) Int. Cl.[7] ............................. G01N 33/53; C12N 5/06; C07K 16/00; A61F 13/00

(52) U.S. Cl. ................. 435/7.1; 435/343.2; 530/388.75; 424/422

(58) Field of Search ................................. 435/7.1, 343.2; 530/388.75; 424/422

(56) References Cited

U.S. PATENT DOCUMENTS

| | | | |
|---|---|---|---|
| 5,709,843 | 1/1998 | Reisner | 424/9.2 |
| 5,869,049 | 2/1999 | Noelle et al. | 424/154.1 |

FOREIGN PATENT DOCUMENTS

| | | |
|---|---|---|
| WO 93/13785 | 7/1993 | (WO) . |
| WO 94/26289 | 11/1994 | (WO) . |
| WO 95/34320 | 12/1995 | (WO) . |
| WO 97/34633 | 9/1997 | (WO) . |
| WO 97/41863 | 11/1997 | (WO) . |
| WO 98/03670 | 1/1998 | (WO) . |

OTHER PUBLICATIONS

Blazar et al., "Blockade of CD40 Ligand–CD40 Interaction Impairs . . . " The Journal of Immunology, vol. 158, No. 1, Jan. 1997, pp. 29–39.

Turka et al., "Blocking B7–1, B7–2 and 1–13 CD40 Costimulatory Pathways . . . " Journal of the American Society of Nephrology, vol. 6, No. 3, 1995, p. 1066.

Sun et al., "Prevention of Chronic Rejection in Mouse Aortic Allografts by Combined Treatment . . . " Transplantation, vol. 64, No. 12, Dec. 1997, pp. 1838–1843.

Lu et al., "Blockade of the CD40–CD40 Ligand Pathway Potentiates the Capacity of Donor–Derived . . . " Transplantation, vol. 64, No. 12, Dec. 1997, pp. 1808–1815.

Wekerle et al., "Extrathymic T Cell Deletion and Allogeneic Stem Cell Engraftment Induced . . . " The Journal of Experimental Medicine, vol. 187, No. 12, Jun. 1998, pp. 2037–2044.

Resetkova et al., "Antibody to gp39, the Ligand for CD40 Significantly Inhibits . . . " Thyroid, vol. 6, No. 4, Aug. 1996, pp. 267–273.

Roy et al., "Studies on the Interdependence of gp39 and B7 Expression . . . " European Journal of Immunology, vol. 25, No. 2, Feb. 1995, pp. 596–603.

Lu et al., "Xenotransplantation," The FASEB Journal, vol. 8, 1994, pp. 1122–1130.

Larsen, C.P., et al., (1996) "Long–term acceptance of skin and cardiac allografts after blocking CD40 and CD28 pathways," Nature 381: pp. 434–438.

Parker, D.C. et al., (1995) "Survival of mouse pancreatic islet allografts in recipients treated with allogenic small lymphocytes and antibody to CD40 ligand," Proc Natl Acad Sci USA, 92: 9560–9564.

(List continued on next page.)

Primary Examiner—Hankyel T. Park
(74) Attorney, Agent, or Firm—Hale and Dorr LLP

(57) ABSTRACT

Use of the blockade of costimulation and hematopoietic stem cells in allograft transplantation.

13 Claims, 5 Drawing Sheets

OTHER PUBLICATIONS

Figure 2A:
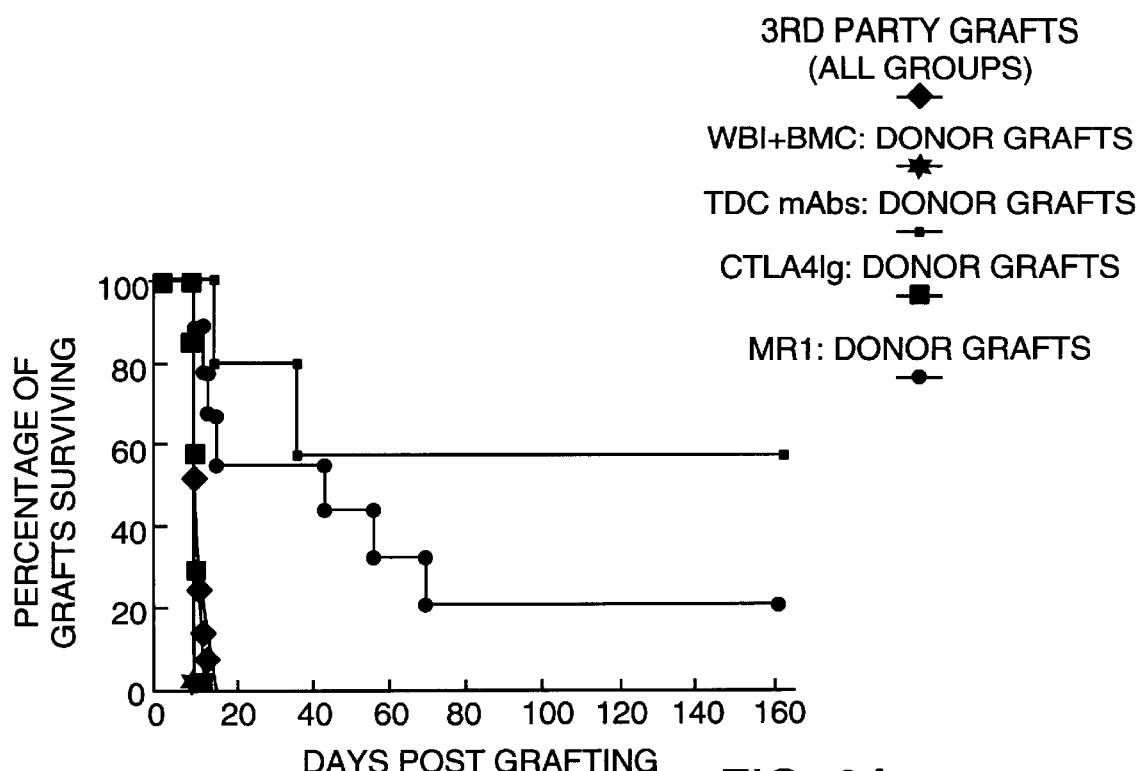

Kirk A.D. et al. (1997) "CTLA4–lg and anti–CD40 ligand prevent renal allograft rejection in primates," Proc Natl Acad Sci USA 94 (Aug.): 8789–8794.

Markees, T.G. et al.,(1997) "Prolonged survival of mouse skin allografts in recipients treated with donor splenocytes and antibody to CD40 ligand," Transplantation 64(2): 329–335.

Larsen, C.P., et al., (1996) "CD40–gp39 interactions play a critical role during allograft rejection. Suppression of allograft rejection by blockade of the CD40–gp39 pathway," Transplantation 61(1): 4–9.

Elwood, E.T., et al., (1998) "Prolonged acceptance of concordant and discordant xenografts with combined CD40 and CD28 pathway blockade," Transplantation 65(11): 1422–1428.

Judge, T.A., et al., (1999) "The Role of CD80, CD86, and CTLA4 in Alloimmune Responses and the Induction of Long–Term Allograft Survival," J Immunol 162(4): 1947–1951.

Blazar, B.R., et al., (1994) "In vivo blockade of CD28/CTLA4: B7/BB1 interaction with CTLA4–lg reduces lethal murine graft–versus–host disease across the major histocompatibility complex barrier in mice," Blood 83(12): 3815–25.

Azuma, H., et al., (1996) "Blockade of T–cell costimulation prevents development of experimental chronic renal allograft rejection [see comments]," Proc Natl Acad Sci USA 93(22): 12439–44.

Hancock, W.W., et al., (1996) "Costimulatory function and expression of CD40 ligand, CD80, and CD86 in vascularized murine cardiac allograft rejection," Proc Natl Acad Sci USA 93(24): 13967–72.

Akalin, E., et al., (1996) "CD28–B7 T cell costimulatory blockade by CTLA4g in the rat renal allograft model: inhibition of cell–mediated and humoral immune responses in vivo," Transplantation 62(12): 1942–5.

Zheng, X.X., et al., (1997) "The role of donor and recipient B7–1 (CD80) in allograft rejection," J Immunol 159(3): 1169–73.

Sayegh, M.H., et al., (1997) "Donor antigen is necessary for the prevention of chronic rejection in CTLA4lg–treated murine cardiac allograft recipients," Transplantation 64(12): 1646–50.

Lin, H., et al., (1993) "Long–term acceptance of major histocompatibility complex mismatched cardiac allografts induced by CTLA4lg plus donor–specific transfusion," J Exp Med 178(5) 1801–6.

Pearson, T.C., et al., (1997) "Analysis of the B7 costimulatory pathway in allograft rejection," Transplantation 63(10): 1463–9.

Pearson, T.C., et al., (1994) "Transplantation tolerance induced by CTLA4–lg [see comments]," Transplantation 57(12): 1701–6.

Lenschow, D.J. et al., (1995) "Inhibition of Transplant Rejection Following Treatment With Anti–B7–2 and Anti–B7–1 Antibodies", Transplantation, vol. 60, No. 10, pp. 1171–1178.*

Lenschow, D.J. et al. (1992) "Long–Term Survival of Xenogeneic Pancreatic Islet Grafts Induced by CTLA4lg", Science, vol. 257 (5071): 789–92.*

Larsen, C. P. et al. (1997) "The CD40 Pathway in Allograft Rejection, Acceptance, and Tolerance", Curr. Opin. Immunol. 9(5): 641–47.*

Lakkis, F.G. et al. (1997) "Blocking the CD28–B7 Cell Costimulation Pathway Induces Long Term Cardiac Allograft Acceptance in the Absence of IL–4[1]", Immunol. 158(5): 2443–48.*

* cited by examiner

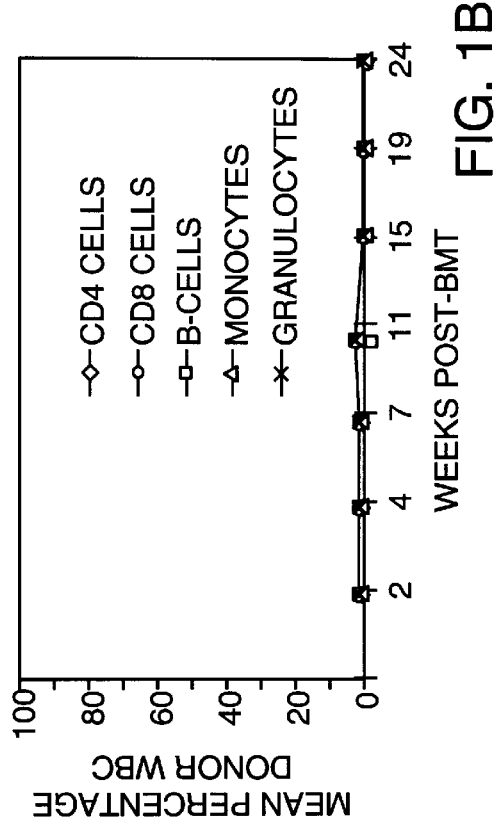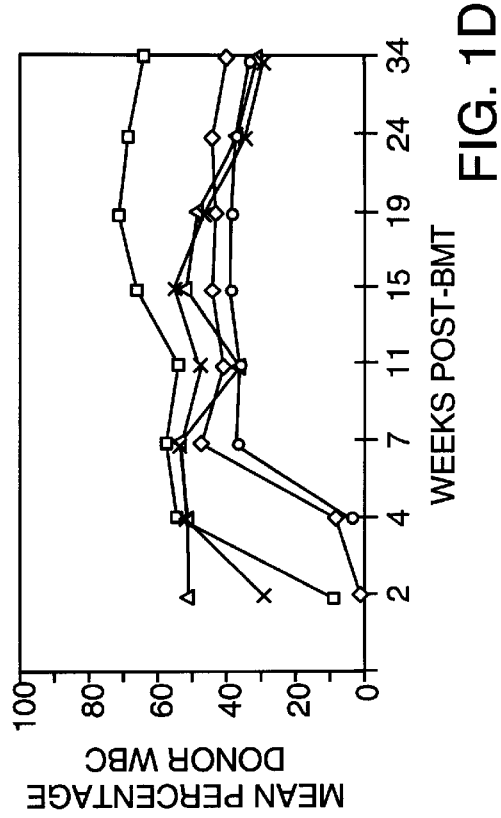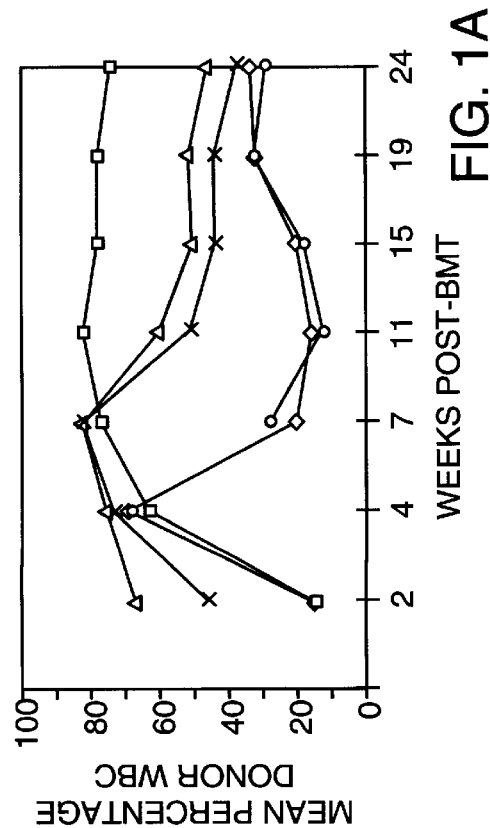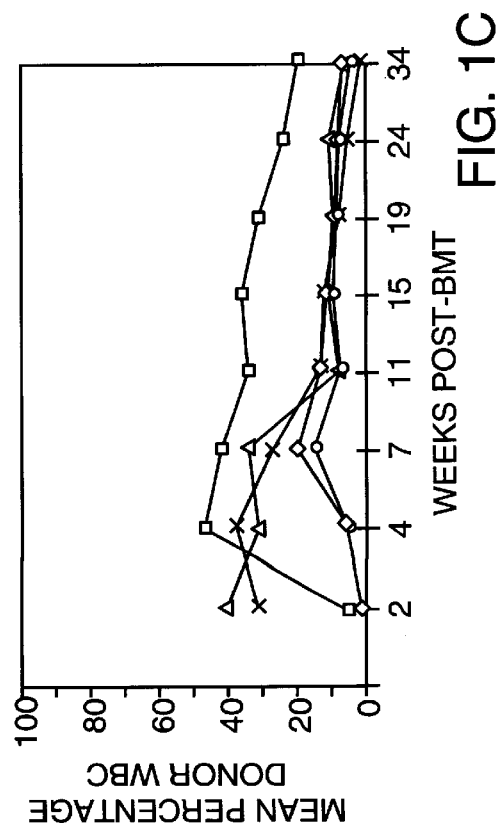

*p<0.05
**p<0.01
***p<0.001
****p<0.0001
*****p<0.00001

- ■ WBI+BMC
- △ CTLA4Ig
- ○ MR1
- ◆ MR1 PLUS CTLA4Ig

US 6,280,957 B1

COSTIMULATORY BLOCKADE AND MIXED CHIMERISM IN ALLO-TRANSPLANTATION

This application claims benefit to provisional application 60/073,864 filed Feb. 4, 1998.

BACKGROUND OF THE INVENTION

The invention relates to tissue and organ transplantation.

The field of organ transplantation has enjoyed substantial progress during the last two decades, resulting in marked improvements in short-term graft survival. Organ transplant recipients, however, still face substantial risks of long-term morbidity and mortality. Though modern immunosuppressive regimens have led to a dramatic reduction of the incidence of acute rejection episodes, they have yet to achieve a similar effect for chronic rejection, which is still the leading cause of graft loss during long-term follow-up. In addition, the requirement for life-long immunosuppressive drug therapy carries a significant risk of severe side effects, including tumors, infections and metabolic disorders. The reliable induction of donor-specific tolerance would solve both problems by obviating the need for chronic non-specific immunosuppression and by abrogating detrimental immunological reactions against the allograft.

SUMMARY OF THE INVENTION

The invention provides methods of inducing tolerance to allo-antigens. The methods feature preparative regimens which minimize or eliminate the need for one or both of thymic irradiation and T cell inhibiting antibodies.

Accordingly, the invention features a method of promoting acceptance, by a recipient mammal, e.g., a primate, e.g., a human, of a graft from a donor mammal of the same species. The method includes:

administering to the recipient, an inhibitor, e.g., a blocker, of the CD40 ligand-CD40 interaction (optionally, an inhibitor or blocker of the CD28-B7 interaction can also be administered);

introducing, e.g., by intravenous injection, into the recipient mammal, hematopoietic stem cells, e.g., a bone marrow preparation; and preferably, implanting the graft in the recipient. The hematopoletic cells are believed to prepare the recipient for the graft that follows, by inducing tolerance at both the B-cell and T-cell levels.

In preferred embodiments the CD40 ligand-CD40 interaction is inhibited by administering an antibody or soluble ligand or receptor for the CD40 ligand or CD40, e.g., by administering an anti-CD40L antibody, e.g., 5c8 or an antibody with similar efficacy or an antibody which has an epitope which overlaps the epitope of 5c8 (see U.S. Pat. No. 5,474,711, hereby incorporated by reference). Preferably the inhibitor binds the CD40 ligand.

In embodiments wherein the CD28-B7 interaction is inhibited, it can be inhibited by administering a soluble ligand or receptor or antibody for the CD28 or B7, e.g., a soluble CTLA4, e.g., a CTLA4 fusion protein, e.g., a CTLA4 immunoglobulin fusion, e.g., a CTLA4/Ig. Preferably, the inhibitor binds B7. In preferred embodiments anti-B7-1 and/or anti-B7-2 antibodies are administered.

In preferred embodiments CTLA4-Ig and an anti CD40L antibody are administered.

In preferred embodiments the donor and recipient both are humans.

In preferred embodiments, a blocker of the CD40/CD40L interaction, e.g., an anti-CD40L antibody is administered prior to administration of a blocker of the CD28/B7 interaction, e.g., CTLA4/Ig. The CD40/CD40L blocker can be administered on the day donor tissue is introduced and the CD28/B7 blocker administered 2, 3, 4, 5 or more days later.

The graft preferably expresses a major histocompatibility complex (MHC) antigen, preferably a class II antigen.

In certain embodiments the method is practiced without T cell depletion or inactivation, e.g., without the administration of thymic irradiation, or anti-T cell antibodies.

In certain embodiments the method is practiced with T cell depletion or inactivation, e.g., by the administration of thymic irradiation, or anti-T cell antibodies.

In certain embodiments the method is practiced with partial T cell depletion or inactivation, e.g., by the administration of thymic irradiation, or anti-T cell antibodies, in such amount to result in partial depletion of recipient T cells.

One or more post graft-implantation-administration of donor stem cells can also be provided. Post graft administration of hematopoietic stem cells can be provided: at least two days, one week, one month, or six months after the previous administration of stem cells; at least two days, one week, one month, six months, or at any time in the life span of the recipient after the implantation of the graft; when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC'S, e.g. when the donor specific monoclonal stains less than 1–2% of the cells; or generally, as is needed to maintain tolerance or otherwise prolong the acceptance of a graft.

Although methods in which blockers of both pathways are administered may usually eliminate the need for other preparative steps, some embodiments include inactivating T cells, preferably graft reactive T cells of the recipient mammal. This can be accomplished, e.g., by introducing into the recipient mammal an antibody capable of binding to T cells of the recipient mammal. The administration of antibodies, or other treatment to inactivate T cells, can be given prior to introducing the hematopoictic stem cells into the recipient mammal or prior to implanting the graft in the recipient.

Monoclonal preparations can be used in the methods of the invention.

Other preferred embodiments include: the step of introducing into the recipient mammal, donor species-specific stromal tissue, preferably hematopoietic stromal tissue, e.g., fetal liver or thymus. In preferred embodiments: the stromal tissue is introduced simultaneously with, or prior to, the hematopoietic stem cells; the hematopoietic stem cells are introduced simultaneously with, or prior to, the antibody.

Although methods in which blockers of both pathways are administered may usually eliminate the need for other preparative steps, some embodiments include the inactivation of thymocytes or T cells, which can be performed prior to hematopoietic stem cell or graft transplantation. In preferred embodiments the method includes diminishing or inhibiting thymocyte or T cell activity, preferably the activity of thymic or lymph node T cells by administering to the recipient a short course of an immunosuppressive agent, e.g., a chemical or drug, e.g., cyclosporine, sufficient to inactivate thymocytes or T cells, preferably thymic or lymph node T cells. The duration of the short course of immunosuppressive agent is: approximately equal to or less than 30, 40, 60, 120, or 365 days; approximately equal to or less than 8–12 days, preferably about 10 days; approximately equal to or less than two, three, four, five, or ten times the 8–12 or 10 day period. The short course can begin: before or at about the time the treatment to induce tolerance is begun, e.g., at about the time stem cells are introduced into the recipient; on the day the treatment to induce tolerance is begun, e.g., on the day stem cells are introduced into the recipient; within 1, 2, 4, 6, 8, 10, or 30 days before or after the treatment to induce tolerance is begun, e.g., within 1, 2, 4, 6, 8, 10, or 30 days before or after stem cells are introduced into the recipient. The short course of an immunosuppressive can be administered in conjunction with an anti-T cell antibody The short course of an immunosuppressive should be sufficient in concentration and duration to inactivate T cells, e.g., thymic or lymph node T cells, which would not be inactivated by antibody-based inactivation of T cells, e.g., inactivation by intravenous administration of ATG antibody, or similar, preparations.

Other preferred embodiments include those in which: the same mammal is the donor of one or both the graft and the hematopoietic cells; and the antibody is an anti- human thymocyte polyclonal anti-serum, obtained, e.g., from a horse or pig.

In preferred embodiments, the method includes the step of introducing into a human recipient, a graft obtained from the donor which is obtained from a different organ than the hematopoietic stem cells, e.g., a heart, pancreas, liver, or kidney.

In a preferred embodiment the method includes creating hematopoietic space, e.g., by irradiating the recipient with low dose of whole body irradiation sufficient to allow formation of mixed hematopoietic chimerism, e.g., less than 400, e.g., 300 cGy, of whole body irradiation to partially deplete the bone marrow of the recipient. Other methods of creating hematopoietic space, e.g., administering hematopoietic space creating antibodies or drugs, e.g., cyclophosphamide or busulfan, to the recipient, can be used. E.g., hematopoictic space can be formed by administering an inhibitor of cell proliferation, e.g., DSG, or an anti-metabolite, e.g. brequinar, or an anti-T cell antibody, e.g., one or both of an anti-CD4 or anti-CD8 antibody.

In a particularly preferred embodiment the method includes:

administering to a human recipient, a blocker of the CD40 ligand-CD40 interaction (optionally, a blocker of the CD28-B7 interaction can also be administered);

introducing, e.g., by intravenous injection, into the recipient mammal, hematopoietic stem cells, e.g., a bone marrow preparation; and implanting the graft in the.

The method can be practiced without T cell depletion or inactivation, with T cell depletion or inactivation, or with partial T cell depletion or inactivation. T cell inactivation can be effected by the administration of thymic irradiation, or anti T cell antibodies.

In preferred embodiments donor tissue, e.g., hematopoietic cells, are depleted, e.g., partially or wholly, of donor T cells.

In a preferred embodiment the administration of costimulatory blockade, and preferably of any needed irradiation or T cell depletion, is administered within 48, more preferably, within 24, hours of implantation of the graft.

"Graft", as used herein, refers to a body part, organ, tissue, or cells. Organs such as liver, kidney, heart or lung, or other body parts, such as bone or skeletal matrix, tissue, such as skin, intestines, endocrine glands, or progenitor stem cells of various types, are all examples of grafts.

"Hematopoietic stem cell", as used herein, refers to a cell, e.g., a bone marrow cell, or a fetal liver or spleen cell, which is capable of developing into all myeloid and lymphoid lineages and by virtue of being able to self-renew can provide long term hematopoietic reconstitution. Purified preparations of hematopoietic cells or preparations, such as bone marrow, which include other cell types, can be used in methods of the invention. Although not wishing to be bound by theory, it is believed that the hematopoietic stem cells home to a site in the recipient mammal. The preparation should include immature cells, i.e., undifferentiated hematopoietic stem cells; these desired cells can be separated out of a preparation or a complex preparation can be administered. E.g., in the case of bone marrow stem cells, the desired primitive cells can be separated out of a preparation or a complex bone marrow sample including such cells can be used. Hematopoietic stem cells can be from fetal, neonatal, immature or mature animals. Stem cells derived from the cord blood of the recipient or the donor can be used in methods of the invention. See U.S. Pat. No. 5,192,553, hereby incorporated by reference, and U.S. Pat. No. 5,004, 681, hereby incorporated by reference. Donor peripheral blood hematopoietic stem cells are preferred.

"Immunosuppressive agent capable of inactivating thymic or lymph node T cells", as used herein, is an agent, e.g., a chemical agent, e.g., a drug, which, when administered at an appropriate dosage, results in the inactivation of thymic or lymph node T cells. Examples of such agents are cyclosporine, FK-506, and rapamycin. Anti-T cell antibodies can also be used. An agent should be administered in sufficient dose to result in significant inactivation of thymic or lymph node T cells which are not inactivated by administration of an anti-T cell antibody, e.g., an anti-ATG preparation. Putative agents, and useful concentrations thereof, can be prescreened by in vitro or in vivo tests, e.g., by administering the putative agent to a test animal, removing a sample of thymus or lymph node tissue, and testing for the presence of active T cells in an in vitro or in vivo assay. Such prescreened putative agents can then be further tested in transplant assays.

"Thymic or lymph node or thymocytes or T cell", as used herein, refers to thymocytes or T cells which are resistant to inactivation by traditional methods of T cell inactivation, e.g., inactivation by a single intravenous administration of anti-T cell antibodies, e.g., anti-bodies, e.g., ATG preparation.

"Thymic irradiation", as used herein, refers to a treatment in which at least half, and preferably at least 75, 90, or 95% of the administered irradiation is targeted to the thymus. Whole body irradiation, even if the thymus is irradiated in the process of delivering the whole body irradiation, is not considered thymic irradiation.

"MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes.

"Hematopoietic space-creating irradiation", as used herein, refers to irradiation directed to the hematopoietic tissue, i.e., to tissue in which stem cells are found, e.g., the bone marrow. It is of sufficient intensity to kill or inactivate a substantial number of hematopoietic cells. It is often given as whole body irradiation.

"Short course of a immunosuppressive agent", as used herein, means a transitory non-chronic course of treatment. The treatment should begin before or at about the time the treatment to induce tolerance is begun, e.g., at about the time stem cells are introduced into the recipient. e.g., the short course can begin on the day the treatment to induce tolerance is begun, e.g., on the day stem cells are introduced into the recipient or the short course can begin within 1, 2, 4, 6, 8, or 10 days before or after the treatment to induce tolerance is begun, e.g., within 1, 2, 4, 6, 8, or 10 days before or after stem cells are introduced into the recipient. The short course can last for: a period equal to or less than about 8–12 days, preferably about 10 days, or a time which is approximately equal to or is less than two, three, four, five, or ten times the 8–12 or 10 day period. Optimally, the short course lasts about 30 days. The dosage should be sufficient to maintain a blood level sufficient to inactivate thymic or lymph node T cells. A dosage of approximately 15 mg/kg/day has been found to be effective in primates.

"Stromal tissue", as used herein, refers to the supporting tissue or matrix of an organ, as distinguished from its functional elements or parenchyma.

"Promoting acceptance of a graft" as used herein, refers to any of increasing the time a graft is accepted or is functional or decreasing the recipients immune response to the graft, e.g., by the induction of tolerance.

"Tolerance", as used herein, refers to an inhibition of a graft recipient's immune response which would otherwise occur, e.g., in response to the introduction of a nonself MHC antigen into the recipient. Tolerance can involve humoral, cellular, or both humoral and cellular responses. Tolerance, as used herein, refers not only to complete immunologic tolerance to an antigen, but to partial immunologic tolerance, i.e., a degree of tolerance to an antigen which is greater than what would be seen if a method of the invention were not employed. Tolerance, as used herein, refers to a donor antigen-specific inhibition of the immune system as opposed to the broad spectrum inhibition of the immune system seen with immunosuppressants.

"A blocker" as used herein, refers to a molecule which binds a member of a ligand/counter-ligand pair and inhibits the interaction between the ligand and counter-ligand or which disrupts the ability of the bound member to transduce a signal. The blocker can be an antibody (or fragment thereof) to the ligand or counter ligand, a soluble ligand (soluble fragment of the counter ligand), a soluble counter ligand (soluble fragment of the counter ligand), or other protein, peptide or other molecule which binds specifically to the counter-ligand or ligand, e.g., a protein or peptide selected by virtue of its ability to bind the ligand or counter ligand in an affinity assay, e.g., a phage display system.

"Partial T cell depletion", as used herein, refers to a condition in which some, but not all, of the subject's T cells are deleted. In some regimens the administration of a single dose of a T cell depleting agent is useful for creating partial T cell depletion.

The use of the article "a" or "an" is non limiting with regard to number except where clearly indicated to be limited by the context. E.g., methods which include administering "an" inhibitor can include administering one or more than one inhibitor.

Methods of the invention minimize or eliminate the need for thymic irradiation.

The invention provides a reliable, non-toxic method of inducing transplantation tolerance. It minimizes the problems of chronic organ graft rejection and immunosuppression-related toxicity. BMT with CTLA4Ig plus MR1 specifically minimizes or eliminates donor-reactive T cells, while avoiding the non-specific depletion or suppression of T cells, which is a component of clinically available immunosuppressive strategies, and can lead to severe complications. This treatment protocol is suitable for both cadaveric and living-related organ transplantation, as it allows the reliable induction of deletional tolerance with a non-toxic conditioning regimen beginning on the day of transplantation. Since the peripheral T cell repertoire is not globally depleted by the conditioning and only a low, minimally myelosuppressive dose of whole body irradiation is given, the clinical usefulness of this approach is extraordinarily high.

Other features and advantages of the invention will be apparent from the following detailed description, and from the claims.

DETAILED DESCRIPTION

DRAWINGS

The drawings are first briefly described.

Figure 4A:
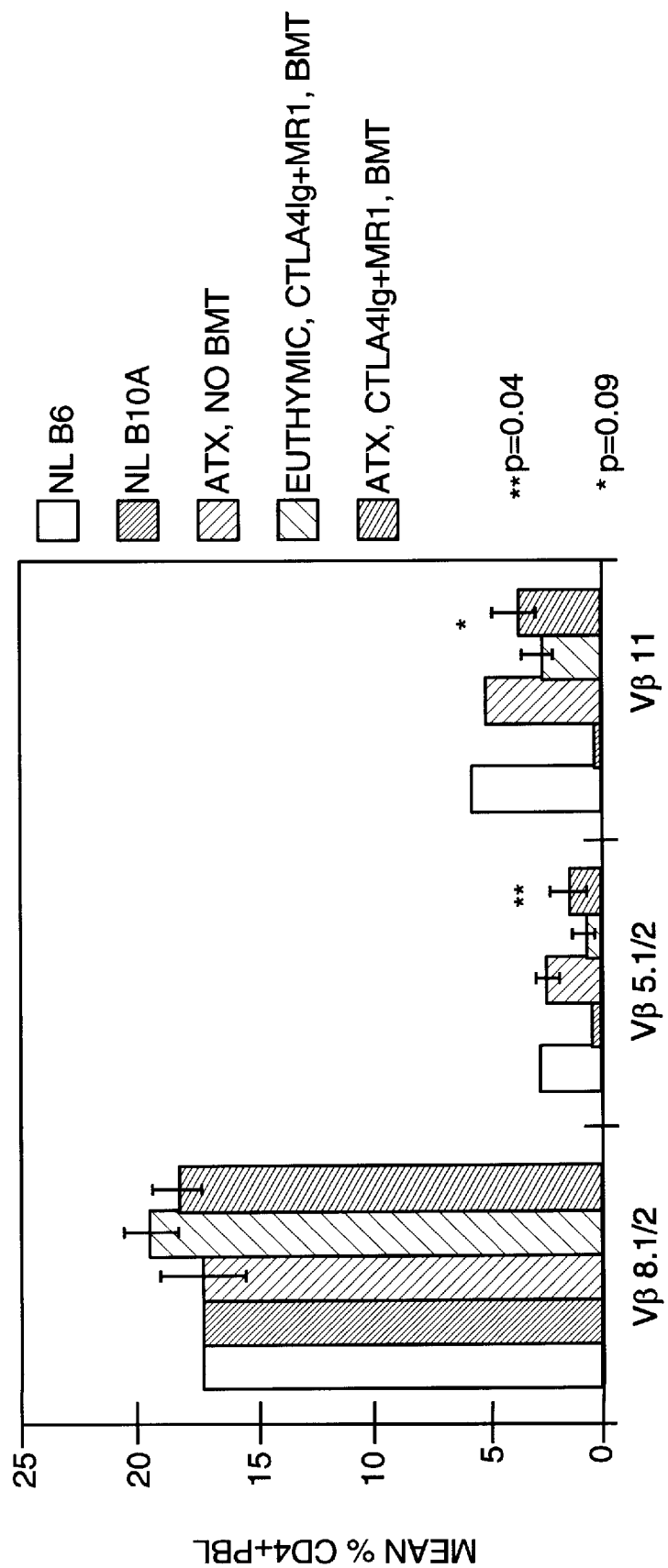
Figures 1, 4B:
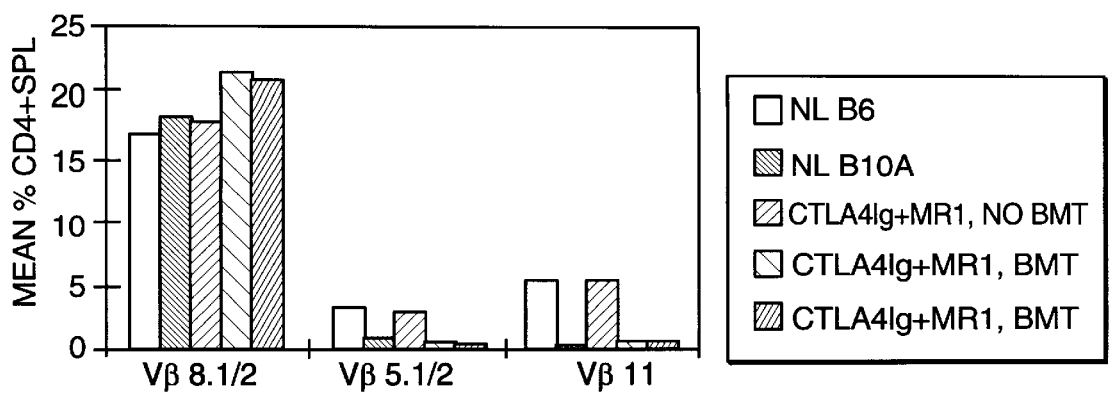

FIG. 1 is a plot of the percentage of donor WBC versus time after BMT. High levels of multi-lineage donor chimerism was seen in peripheral blood for 34 weeks after BMT. Results from one of two similar experiments are shown as group averages. All animals received 3 Gy WBI and 15×106 allogeneic BMC on day 0. Only MR1 plus CTLA4Ig together (D) allowed the reliable induction of stable chimerism (n=5), with high levels of donor cells in all lineages throughout the follow-up. Administration of MR1 alone (C) led to significant levels of chimerism, but chimerism declined over time (n=5). When CTLA4Ig was given alone (B), no chimerism was detectable by FCM (n=4). A control group (n=5), receiving depleting doses of anti-CD4 and anti-CD8 mAbs on d-5 and d-1 (A), showed substantial levels of donor chimerism, with plateau levels of T cell chimerism being significantly lower, however, than B cell, granulocyte and monocyte chimerism.

Figures 2, 4B:
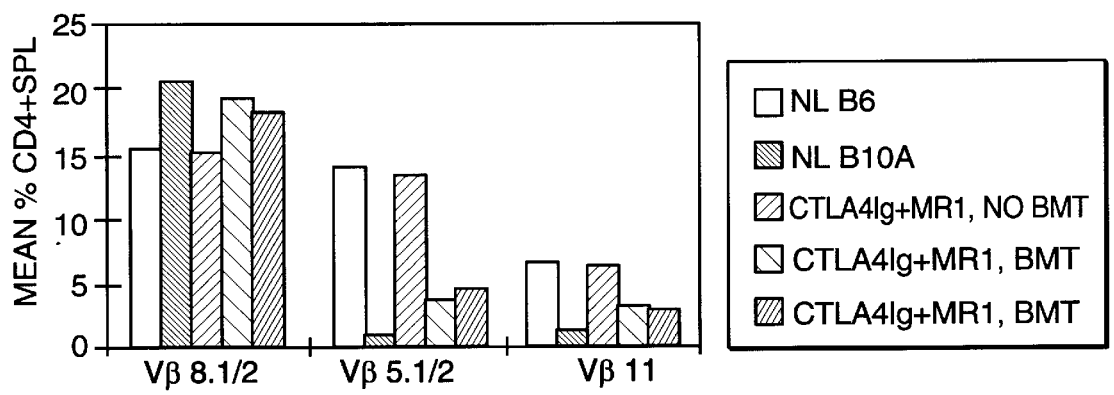

FIG. 2 is a plot of graft survival versus day past grafting. Permanent survival of donor-specific skin grafts in chimeras prepared with 3 Gy WBI and allogeneic (B10.A) BMC and treatment with MR1 plus CTLA4Ig was seen. Combined results from two experiments are shown. Recipients were grafted with donor-specific (B10.A) and third party (A.SW) skin grafts at 3, 6 or 10 weeks after BMT. Mice receiving the full treatment of BMT and MR1 plus CTLA4Ig accepted donor skin grafts (B) permanently (12 out of 14), with the exception of two animals that rejected their grafts at days 57 and 76, respectively. Nine grafts have been accepted in perfect condition for more than 110 days, and 5 grafts for more than 140 days. Third-party skin grafts (B) were rejected in the expected time-frame (MST)=10d). MR1 alone (A) led to prolongation of donor-specific skin graft survival (MST=42d), but only 2 out of 9 grafts survived more than 100 days. CTLA4Ig alone (A) failed to improve skin graft survival (n=7, MST=10d). Control mice treated with 3 Gy WBI plus BMC (n=4) and mice receiving 3 Gy WBI and MR1 plus CTLA4Ig alone (without BMT, not shown) rejected donor skin within 2 weeks. A control group prepared with TCD mAbs on d-5 and d-1 plus BMT (+3 Gy WBI) (n=5), accepted donor skin grafts permanently in 60%. Third party grafts were rejected within 2 weeks in all groups.

Figures 3, 4B:
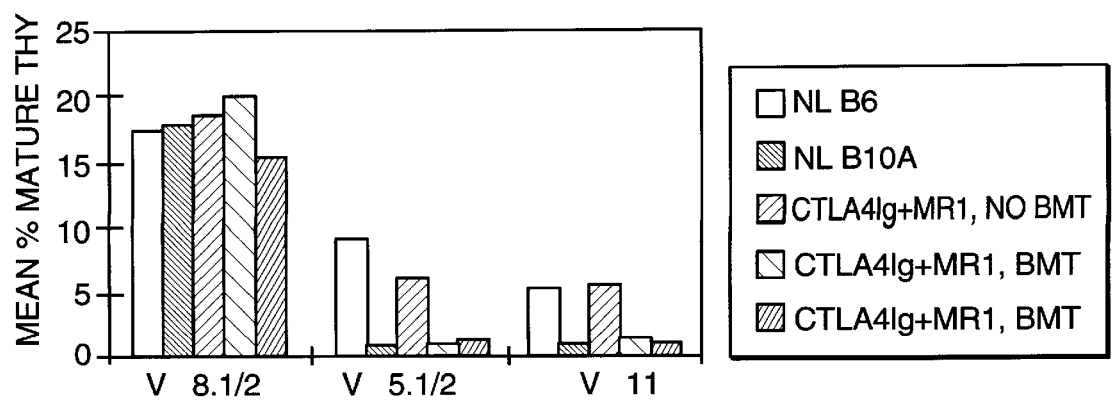

FIG. 3 is a depiction of specific deletion of donor-reactive peripheral T cells in recipients of BMT and MR1 plus CTLA4Ig. Results from one of two similar experiments are shown. FCM analysis was performed at indicated time points, with the percentage of Vβ-positive cells being determined among gated CD4-positive PBL. The mean percentage of CD4+ lymphocytes expressing Vβ5½ or Vβ11 was significantly lower in mice receiving BMC (+3 Gy WBI) with MR1 plus CTLA4Ig (n=10) than in recipients of BMC (+3 Gy WBI) alone (n=4), as early as 1 week after BMT ($P<0.01$ for Vβ11, $P<0.05$ for Vβ5). The donor specific deletion gradually became more complete at 3, 5 and 8 weeks after BMT and was sustained for the length of follow-up. The percentage of Vβ8½+ CD4 cells remained similar in all groups, demonstrating specificity of the Vβ5½ or Vβ11 deletion in mixed chimeras. Mice receiving BMC (+3 Gy WBI) alone or in addition to CTLA4Ig (n=4) did not show any deletion, nor did control mice treated with MR1 plus CTLA4Ig alone (without BMC, not shown). MR1 alone led only to a slight and transient deletion in this experiment (n=5). Error bars indicate standard deviation. P values are shown for comparison with the control group receiving 3 Gy WBI plus BMC. NL B6 denotes naive C57BL/6 control, NL B10.A denotes naive B10.A control.

FIG. 4 is a depiction of extrathymic clonal deletion after BMT and costimulatory blockade with CTLA4Ig and MR1. A: ATX recipients (n=6) showed specific, partial deletion of Vβ5½ and Vβ11 positive CD4 cells in PBL, one week after BMT plus CTLA4Ig and MR1. A similar degree of deletion was observed in euthymic controls (n=5) prepared with the same conditioning. CD4 cells in ATX controls receiving CTLA4Ig plus MR1 and WBI without BMT (n=4) did not show deletion of these Vβ. The percentage of Vβ positive cells was determined by FCM analysis of gated CD4-positive PBL. P-values are shown for comparison between ATX BMT recipients receiving CTLA4Ig plus MR1 and ATX non-BMT controls. B: In two euthymic chimeras sacrificed 20 weeks post BMT (under cover of 3 Gy WBI, plus treatment with CTLA4Ig plus MR1), Vβ5½+ and Vβ11+ CD4+ splenocytes (SPL) were deleted to the same extent as in naive B10.A controls (top panel). In contrast, the percentage of Vβ5½+ and Vβ11+ CD8+ splenocytes was reduced compared to naive B6 mice, but was substantially higher than in naive B10.A mice (middle panel). Mature Vβ5½+ and Vβ11+ thymocytes (THY) showed deletion comparable to B10.A at the same time (bottom panel). A control mouse receiving WBI and CTLA4Ig plus MR1 (but no BMT) showed no deletion in either splenocytes or thymocytes. The percentage of Vβ positive cells was determined by FCM analysis in gated CD4-positive (or CD8-positive) 34-2-12-negative splenocytes, and in gated KH-95high (i.e. Dd high)-thymocytes (see Materials and Methods). NL B6 denotes naive C57BL/6 control, NL B10.A denotes naive B10.A control.

Sources of Cells for Allogeneic Stem Cell Transplantation

Sources of hematopoietic stem cells include bone marrow cells, mobilized peripheral blood cells, and when available cord blood cells. Mobilized peripheral stem cells are preferred in methods of the invention. In vitro expanded hematopoietic cells can be used in methods of the invention.

The Induction of Tolerance with Bone Marrow Transplantation

The following procedure was designed to lengthen the time an implanted organ survives in an allogeneic host prior to rejection. The organ can be any organ, e.g., a liver, a kidney, a pancreas, or a heart. The method main strategies include: administration of inhibitors of the CD40 ligand-CD40 (and optionally an inhibitor of the CD28-B7 interaction) and transplantation of tolerance-inducing stem cells, e.g., bone marrow stem cells. The method includes any or all of these steps. Preferably they are carried out in the following sequence.

A preparation of anti-CD40 ligand monoclonal antibody and optionally of CTLA4-IgG fusion protein are administered to the subject.

It may also be necessary or desirable to splenectomize the recipient.

Bone marrow cells (BMC), or another source of hematopoictic stem cells, e.g., donor peripheral hematopoietic stem cells, of the donor are injected into the recipient. Donor hematopoietic stem cells home to appropriate sites of the recipient and grow contiguously with remaining host cells and proliferate, forming a chimeric lymphohematopoietic population. By this process, newly forming and pre-existing B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. When an organ graft is placed in such a recipient several months after bone marrow mixed chimerism has been induced the graft should be accepted by both the humoral and the cellular aims of the immune system. This approach has the added advantage of permitting organ transplantation to be performed sufficiently long following transplant of hematopoietic cells, e.g., BMT, e.g., a fetal liver suspension, that normal health and immunocompetence will have been restored at the time of organ transplantation The subject can be exposed to whole body irradiation to create hematopoietic space, e.g., 300 cGy of whole body X-rays.

Finally, T cells, particularly, thymic or lymph node T cells, can be further suppressed by administering to the recipient a short course of an immunosuppressive agent, e.g., cyclosporine.

While any of these procedures may aid the survival of an implanted organ, best results are achieved when all steps are used in combination.

The approaches described above are designed to synergistically prevent the problem of transplant rejection.

The methods of the invention may be employed in combination, as described, or in part.

The method of introducing bone marrow cells may be altered, particularly by (1) increasing the time interval between injecting hematopoietic stem cells and implanting the graft; (2) increasing the amount of hematopoietic stem cells injected; (3) varying the number of hematopoietic stem cell injections; (4) varying the method of delivery of hematopoietic stem cells; (5) varying the tissue source of hematopoietic stem cells, e.g., a fetal liver cell suspension may be used; or (6) varying the donor source of hematopoietic stem cells.

Methods of preparing the recipient for transplant of hematopoietic stem cells may be varied. For instance, recipient may undergo a splenectomy. The latter would preferably be administered prior to the non-myeloablative regimen, e.g., at day −14.

Stromal tissue introduced prior to hematopoietic cell transplant, e.g., BMT, may be varied by: (1) administering the fetal liver and thymus tissue as a fluid cell suspension; (2) administering fetal liver or thymus stromal tissue but not both; (3) placing a stromal implant into other encapsulated, well-vascularized sites, or (4) using adult thymus as a source of stromal tissue.

EXAMPLE 1

In this animal trial, the treatment of mice with single injections of an anti-CD40 ligand-antibody and CTLA4Ig, a low dose (3 Gy) of whole body irradiation, plus fully MHC-mismatched allogeneic bone marrow transplantation reliably induced high levels (>40%) of stable (>8 months) multi-lineage donor hematopoiesis. Chimeric mice permanently accepted donor skin grafts (>100 days), and rapidly rejected third party grafts. Progressive deletion of donor-reactive host T cells occurred among peripheral CD4+ lymphocytes, beginning as early as one week after bone marrow transplantation. Early deletion of peripheral donor-reactive host CD4 cells also occurred in thymectomized, similarly-treated marrow recipients, demonstrating a role for peripheral clonal deletion of donor-reactive T cells after allogencic bone marrow transplantation in the presence of costimulatory blockade. Central intrathymic deletion of newly-developing T cells ensued after donor stem cell engraftment had occurred.

Solid organ (skin) grafting was not required in the induction phase of tolerance in model. Instead, the permanent engraftment of donor hematopoietic cells ensured the tolerization of pre-existing host T cells and of T cells that developed subsequent to the disappearance of the costimulatory blocking agents from the circulation. This later tolerance occurred through intrathymic deletional mechanisms (FIG. 4), presumably as a consequence of the presence of donor-derived APC in the thymus, as has been demonstrated in long-term mixed chimeras prepared with other regimes that involve initial depletion of the T cell repertoire with mAbs. The work described herein shows that costimulatory blockade leads to peripheral deletion of donor-reactive T cells, then allows the engraftment of fully MHC-mismatched, allogeneic pluripotent stem cells, which induce central tolerance among T cells that subsequently develop in the thymus.

This is described in more detail below.

Animals

Female C57BL/6 (B6: H-2b), B10.A (B10.A: H-2a) and A.SW (H-2s) mice were purchased from Frederick Cancer Research Center (Frederick, Md.) or from The Jackson Laboratory (Bar Harbor, Me.). Mice were maintained in a specific pathogen-free microisolator environment, as described in Sykes, M., M. L. Romick, K. A. Hoyles, and D. H. Sachs. 1990, J.Exp.Med. 171:645–658.

Conditioning and Bone Marrow Transplantation

Age-matched (6–8 weeks old) female B6 mice received 3 Gy whole body irradiation (WBI) and were injected intravenously on the same day (d0) with unseparated BM harvested from MHC-mismatched female B10.A donors (10–12 weeks old). A control group was injected i.p. with depleting doses of rat IgG2b anti-mouse CD4 mAb GK1.5 and anti-mouse CD8 mAb 2.43 on days −5 and −1, as described in Sharabi, Y. and D. H. Sachs. 1989, J.Exp.Med. 169:493–502. Murine CTLA4Ig was injected i.p. as a single dose (0.5 mg) on d+2, and hamster anti-mouse CD40L mAb (MR1) was injected i.p. on d0 (0.45 mg). CTLA4Ig was a generous gift of Bristol-Myers, Squibb Pharmaceuticals, Seattle, Wash.; the MR1 hybridoma was kindly provided to us by Dr. Randolph J. Noelle. Thymectomies were performed four weeks prior to BMT. The completeness of thymectomy was confirmed at the time of sacrifice two weeks post-BMT by visual inspection and two-color FACS staining (CD4-FITC versus CD8-PE) of mediastinal tissue. Mice showing any evidence of remaining thymic tissue were excluded from analysis.

Flow Cytometric Analysis of Multi-lineage Chimerism

Flow-cytometric analysis (FCM) of multi-lineage chimerism was performed as previously described in Tomita, Y., D. H. Sachs, A. Khan, and M. Sykes. 1996,Transplantation 61:469–477. Briefly, forward angle and 90 degree light scatter properties were used to distinguish lymphocytes, monocytes and granulocytes in peripheral white blood cells. Two-color FCM was utilized to distinguish donor and host cells of particular lineages, and the percentage of donor cells was calculated as described in Tomita, Y., D. H. Sachs, A. Khan, and M. Sykes. 1996, Transplantation 61:469–477, by subtracting control staining from quadrants containing donor and host cells expressing a particular lineage marker, and by dividing the net percentage of donor cells by the total net percentage of donor plus host cells of that lineage. Dead cells were excluded using propidium iodide staining. Non-specific FcgR binding was blocked by anti-mouse FcgR mAb 2.4G2, Unkeless, J. C. 1979, J.Exp.Med. 150:580–596. Fluorescin isocyanate (FITC)-conjugated mAbs included anti-CD4, anti-CD8, anti-B220 (all purchased from PharMingen, San Diego, Calif.) and anti-MAC1 (Caltag, San Francisco, Calif.). Negative control mAb HOPC1-FITC, with no reactivity to mouse cells, was prepared in our laboratory. Biotinylated anti-H-2Dd mAb 34-2-12 and control mAb HOPC1 were developed with phycoerythrin-streptavidin (PEA).

Flow Cytometric Analysis of T Cell Receptor Vβ Families

Peripheral blood lymphocytes were stained with anti-Vβ5½-FITC, Vβ11-FITC and Vβ8½-FITC mAb versus phycocrythrin-conjugated anti-CD4 mAb (all PharMingen). Non-specific phycoerythrin-conjugated rat IgG2a (PharMingen) served as negative control. Two-color FCM analysis was performed on gated CD4+ cells. Splenocytes (SPL) were stained with anti-Vβ5½-FITC, Vβ11-FITC and Vβ8½-FITC mAb versus phycoerythrin-conjugated anti-CD4 mAb (or anti-CD8 mAb, PharMingen) and versus anti-34-2-12-BIO developed with CyChrome-streptavidin (CCA, PharMingen). Three-color FCM analysis was performed on 34-2-12-negative, CD4-positive (or CD8-positive) cells. Thymocytes were stained with anti-TCRβ-FITC (PharMingen), anti-Vβ5½-FITC, Vβ11-FITC and Vβ8½-FITC versus anti-KH95-BIO (anti-Db, PharMingen) developed with PEA. Two-color FCM analysis was performed on gated class-I (I(<95)-high cells, and the percentage of Vβ positive cells in this gate was corrected for the percentage of TCR-high cells in the same gate, as described in Tomita, Y., A. Khan, and M. Sykes. 1994, J.Immunol. 153:1087–1098. Background staining (as determined by non-reactive mAb HOPC-FITC) was subtracted from the percentage of cells staining with each anti-Vβ mAb. P values were calculated using a two-tailed Student's T-test.

Skin Grafting

Full thickness tail skin from B10.A (donor-specific) and fully MHC-mismatched A.SW (third party) mice was grafted onto the lateral thoracic wall, secured with 5-0 silk sutures and bandaids and followed by visual and tactile inspections daily for three weeks, then at least every week thereafter. Grafts were defined as rejected when less than 10% of the graft remained viable.

Stable Multi-lineage Hematopoietic chimerism After Treatment with CTLA4Ig Plus Anti-CD40L mAb (MR1)

To determine whether blocking the CD28 and CD40 costimulatory pathways could allow survival of fully MHC-mismatched bone marrow and the induction of mixed chimerism and tolerance, B6 mice were treated with 3 Gy WBI and received 15×106 unseparated bone marrow cells (BMC) from fully MHC-mismatched B10.A donors. A single dose of an anti-CD40L mAb (MR1) and of CTLA4Ig was given either alone or in combination, on days 0 and +2, respectively. Donor hematopoiesis was assessed at multiple timepoints post-BMT by flow-cytometric analysis of peripheral WBC. By staining with a mAb specific for donor class-I versus various lineage markers, the net percentage of donor cells among these lineages was determined.

The combined administration of CTLA4Ig plus MR1 led to high levels of chimerism in all hematopoietic lineages, including T cells, B cells and myeloid cells (FIG. 1D). Donor reconstitution averaged more than 40% in all lineages by 7 weeks, and remained high during the observation period of 34 weeks. Especially surprising was the high level of donor representation among CD4 and CD8 cells by 7 weeks post BMT, even though the hosts did not receive T cell depletion in their conditioning. Donor T cell levels in the group treated with MR1 plus CTLA4Ig were stable throughout long-term follow-up (34 weeks) and were, on average, higher than those in a control group conditioned with anti-CD4 and anti-CD8 depleting mAbs (FIG. 1A). Fifteen of 16 mice treated with the combination of MR1 and CTLA4Ig developed high levels of chimerism (one mouse showed no detectable chimerism and was excluded from further analysis as an outlier). Treatment with MR1 alone led to high levels of donor cells among myeloid lineages and B cells at early time points post BMT, and to lower levels of chimerism among CD4 and CD8 cells. The induction of chimerism was less reliable than that in the group receiving both costimulatory blocking reagents, however, and donor chimerism was not stable in this group (FIG. 1C). Mice receiving CTLA4Ig alone did not show chimerism in peripheral blood, as detected by FCM, at any time after BMT (FIG. 1B). Similarly, control animals receiving WBI and BMC alone failed to show hematopoietic chimerism.

Donor-specific Skin Graft Tolerance in Chimeras Prepared with CTLA4Ig Plus MR1

Figure 2B:
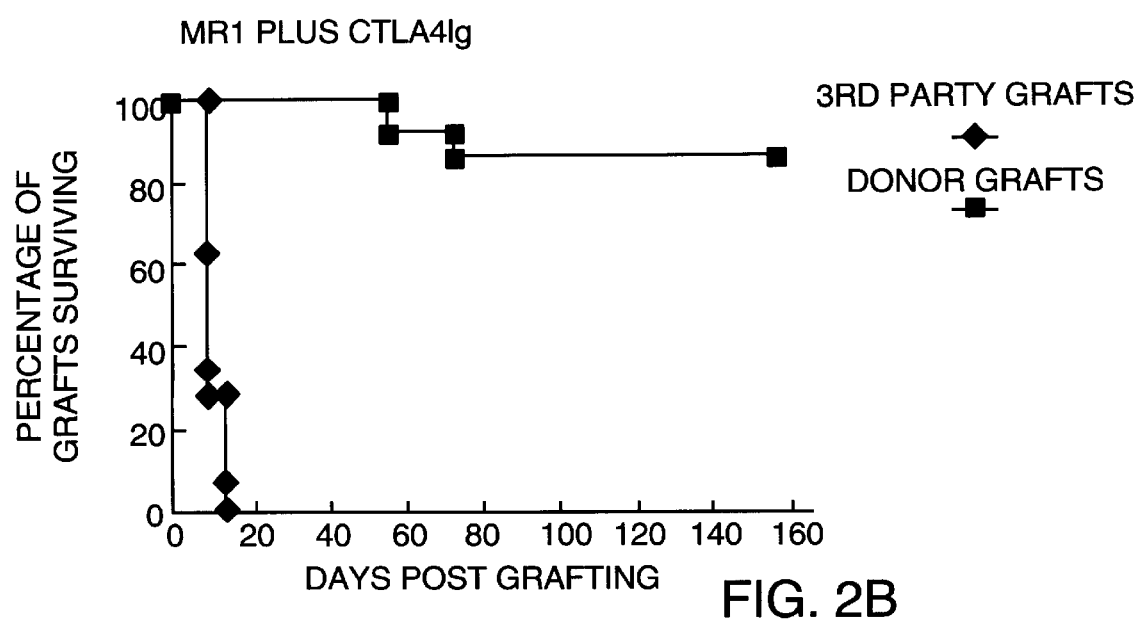
Figure 3A:
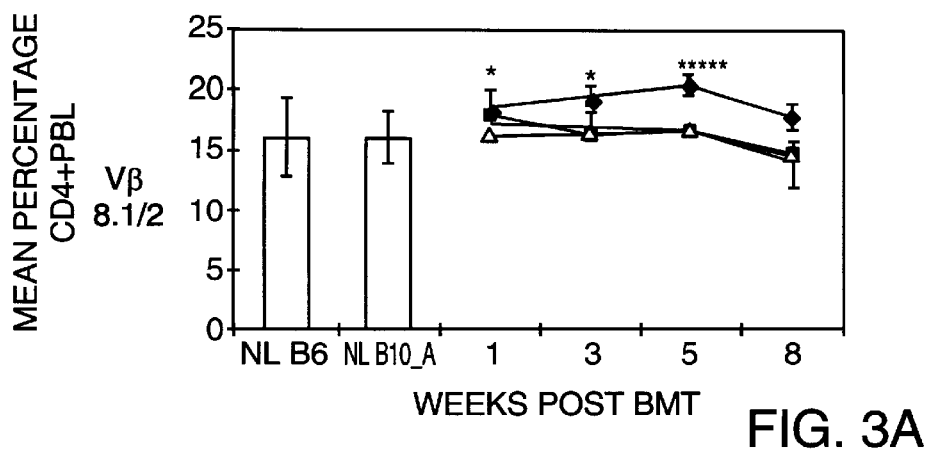
Figure 3B:
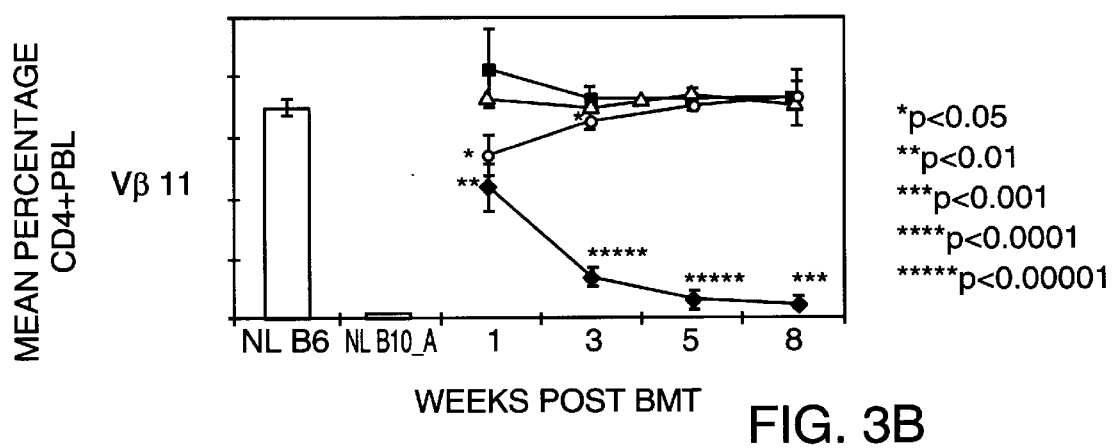
Figure 3C:
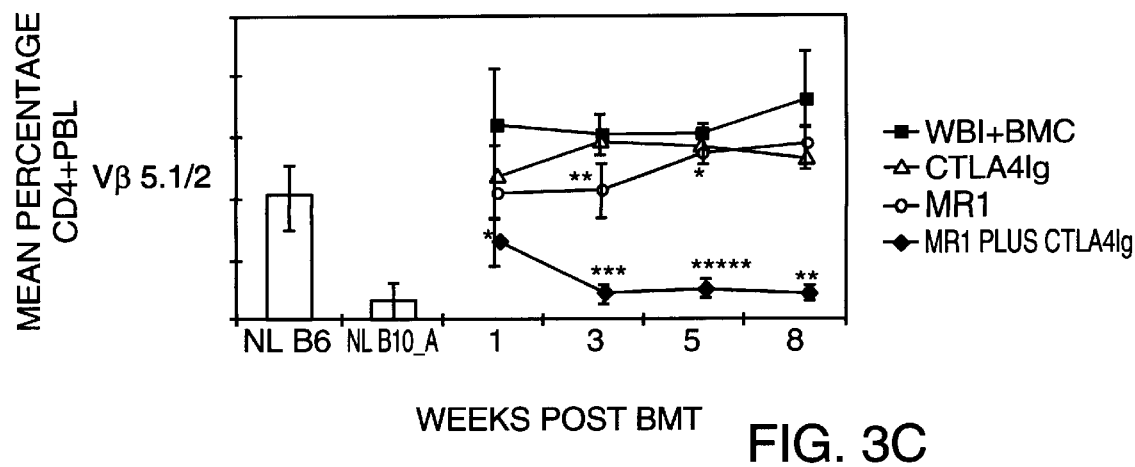

Primary skin grafting is considered the most stringent test of transplantation tolerance. Therefore, donor (B10.A) and third party (A.SW) full-thickness tail skin were grafted onto recipients at various time points after BMT. Mice that received both CTLA4Ig and MR1, plus 3 Gy WBI and BMT, permanently accepted donor skin grafts placed 3, 6 or 10 weeks after BMT (FIG. 2B), with the exception of two animals that rejected their grafts 57 and 76 days after graft placement, respectively. Third party grafts were readily rejected (median survival time (MST)=10d), demonstrating the donor specificity of the tolerance induced. This skin graft survival compares favorably even to the control animals that were conditioned with T cell-depleting antibodies, in which only 60% of donor skin grafts survived more than 100 days (FIG. 2A). Mice treated with MR1 alone in addition to 3 Gy WBI and BMT demonstrated prolongation of donor skin graft survival (MST=42d) (FIG. 2A). However, only 2 out of 9 grafts were accepted for 100 days. In contrast, in this particular protocol, mice receiving BMT following 3 Gy WBI and CTLA4Ig alone did not show prolonged survival of donor skin grafts (MST=10d), consistent with the absence of chimerism.

These results demonstrate the presence of donor-specific tolerance across a full MHC barrier in chimeras prepared with MR1 plus CTLA4Ig. The ability of mixed chimeras prepared with MR1 and CTLA4Ig to rapidly reject third party skin grafts is evidence for their immunocompetence.

Deletion of Donor-reactive T Cells in Chimeras Prepared with CTLA4Ig Plus MR1

To examine whether deletion of donor-reactive T cells occurs when chimerism is induced with MR1 and CTLA4Ig, peripheral blood lymphocytes were analyzed for the presence of certain V$\beta$ subunits on their T cell receptors. The donor strain B10.A expresses I-E, which is required to present superantigens derived from Mammary tumor virus (Mtv)-8 and -9 endogenous retroviruses encoded in the B6/B10 background genome. Developing thymocytes whose T cell receptors contain V$\beta$11 or V$\beta$5½,which bind to these superantigens, are deleted in I-E-positive B10.A mice Acha-Orbea, H. and E. Palmer. 1991, Immunol.Today 12:356–361; Tomonari, K. and S. Fairchild, Immunogenetics 33:157–162; Dyson, P. J., A. M. Knight, S. Fairchild, E. Simpson, and K. Tomonari. 1991, Nature 349:531–532., but not in B6 mice, because they do not express I-E Tomonari, K. and S. Fairchild. 1991, Immunogenetics 33:157–162; Dyson, P. J., A. M. Knight, S. Fairchild, E. Simpson, and K. Tomonari. 1991, Nature 349:531–532; Bill, J., 0. Kanagawa, D. Woodland, and E. Palmer. 1989, J.Exp.Med. 169:1405–1419.

Partial deletion of V$\beta$5+ and V$\beta$11+ peripheral CD4 T cells was observed as early as one week after BMT in mice receiving 3 Gy WBI followed by MR1 plus CTLA4Ig (FIG. 3). The deletion became progressively more complete over the ensuing weeks, and reached similar levels to those in chimeras prepared with T cell depletion (not shown). Deletion of these V$\beta$5+ and V$\beta$11+ cells was sustained throughout the follow-up period (>6 months in the first experiment for which chimerism data are shown in FIG. 1). Percentages of V$\beta$8-bearing CD4 cells, which do not recognize superantigens on the donor or host, were not reduced at any time point, ruling out a non-specific deletional process. Mice treated with BMT (plus 3 Gy WBI) and MR1 alone showed early partial deletion of V$\beta$5 and V$\beta$11, which was only transient in the experiment shown (FIG. 3). However, in the experiment shown in FIG. 1, deletion was still observed at later time points for the group receiving BMT (plus 3 Gy WBI) and MR1 alone, which correlated with the higher initial levels of chimerism observed for this group in this experiment. Control animals receiving 3 Gy WBI plus BMT alone or BMT (plus 3 Gy WBI) with CTLA4Ig failed to show any V$\beta$5 or V$\beta$11 deletion. As expected, deletion of V$\beta$5 and V$\beta$11 did not occur in control animals receiving WBI and MR1 plus CTLA4Ig without BMT (not shown). Down-regulation of the level of TCR expression instead of deletion seems an unlikely explanation for the reduction in V$\beta$5+ and V$\beta$11+ CD4 T cells in chimeras, since the intensity of the V$\beta$5 and V$\beta$11 staining on the cells remaining in the blood at one and three weeks post-BMT was similar to that in non-transplanted controls (data not shown). Thus, no evidence for TCR down-modulation was observed.

These results show that in BMT recipients treated with MR1 plus CTLA4Ig and 3 Gy WBI, donor-reactive host T cells start to disappear from the periphery very soon after BMT. Neither CTLA4Ig nor MR1 is known to be directly cytotoxic to the T cells to which they bind. 3 Gy WBI causes only transient and mild leukopenia and only partial T cell depletion. This time-course suggests that the deletion observed at one week is not entirely due to intrathymic mechanisms, since a sufficient number of thymocytes would be unlikely to emigrate from the thymus during this period to "dilute" the pre-existing peripheral repertoire to an extent that could explain the observed decrease in Vβ5+ and Vβ11+ CD4 lymphocytes in PBL.

Extrathymic Clonal Deletion Occurs in the Early Period After BMT and Costimulatory Blockade To directly determine whether peripheral deletion is responsible for the early decline in donor-reactive CD4 T cells in chimeras, thymectomized (ATX) B6 mice received B10.A BMC after conditioning with 3 Gy WBI and MR1 plus CTLA4Ig. As shown in FIG. 4A, ATX mice demonstrated partial deletion of Vβ5+ and Vβ11+ peripheral blood CD4 cells one week after BMT, and the degree of deletion was comparable to that in euthymic recipients. Vβ8+ CD4 cells were not diminished, indicating the specificity of the deletion for superantigens presented by the donor. Similarly-treated ATX mice not receiving BMT showed no reduction in the percentage of Vβ5+ or Vβ11 CD4 cells compared to untreated B6 mice (FIG. 4A), demonstrating that this peripheral deletion occurred specifically in response to donor marrow in BMT recipients.

Further evidence that peripheral deletion plays a role in the early period after BMT in this model, was obtained from chimeras sacrificed 20 weeks post BMT and CTLA4Ig plus MR1. Among splenocytes of these mice, the percentage of Vβ5+ and Vβ11+ cells among CD4+ T cells was reduced to similar levels as in normal, control B10.A mice. However, the percentages of Vβ5+ and Vβ11+ cells were substantially higher among CD8+ splenocytes than among CD4+ splenocytes. Nevertheless, the percentages of CD8 splenocytes using these Vβ were significantly lower than among those of normal, control B6 mice (FIG. 4B). As discussed below, this difference most likely reflects the dilution of the peripheral CD8 pool by new thymic emigrants which are tolerized by a central deletion mechanism in the chimeras.

Peripheral deletion has been shown to be one consequence of powerful T cell responses in vivo, but it has only been reported following marked expansion of antigen-recognizing cells. Although one week post-transplant was the earliest time point at which donor-reactive host T cells were examined, evidence of such initial expansion was not seen. More recently, in vitro evidence has demonstrated that costimulatory signals play a prominent role in preventing apoptotic cell death following TCR engagement. However, apoptosis induced in vivo by antigen encountered in the presence of costimulatory blockade has not been described.

Evidence for Central Deletion of Donor-reactive T Cells in Long-term Chimeras

Mature recipient T cells (including both CD4 and CD8 cells) in the thymus showed marked deletion of Vβ5 and Vβ11 when animals were sacrificed 20 weeks post-BMT (FIG. 4B), demonstrating that newly developing donor-reactive thymocytes are effectively deleted during maturation in the thymus in long-term chimeras.

Together, these data suggest that extrathymic clonal deletion occurs early after BMT under cover of costimulatory blockade. Allogeneic pluripotent stem cell engraftment is thus permitted and subsequent tolerization of newly-developing donor-reactive thymocytes occurs by deletional mechanisms in the thymus similar to that which occurs in animals initially treated with T cell depleting mAbs. This also explains the discrepancy in the extent of deletion of CD4 cells compared to CD8 cells in the peripheral tissues of long-term chimeras. Vβ5+ and Vβ11+ CD4 cells are subject to deletion both intrathymically and in the periphery when they recognize superantigen plus donor MHC class II. CD8 cells expressing these Vβ are efficiently deleted intrathymically at the CD8+ CD4+ stage of maturation. However, CD8+ CD4− cells are not very effectively deleted extrathymically, even though weak proliferative activity to superantigens presented by class II MHC in the periphery has been described. It follows that the substantial difference in the degree of deletion between peripheral CD4 and CD8 cells is most likely due to the more extensive contribution of extrathymic deletion among the CD4 compared to the CD8 cells pre-existing at the time of BMT. This conclusion is further supported by the observation that ATX recipients of BMT plus costimulatory blockade demonstrated a significant reduction of Vβ5 and Vβ11 positive CD4 splenocytes, but not of CD8 splenocytes at two weeks post-BMT.

EXAMPLE 2

Thymic irradiation (TI) or repeated administration of T cell-depleting mAbs (TCD mAbs) allows allogeneic marrow engraftment with stable mixed chimerism and tolerance. Since both treatments might be associated with toxicity in the clinical setting, we evaluated whether T cell costimulatory blockade could be used to replace them.

C57BL/6 mice received depleting anti-CD4 and anti-CD8 mAbs on day −5, 3 Gy whole body irradiation (WBI, day 0), and $15 \times 10^6$ fully MHC-mismatched, B10.A bone marrow cells (BMC). In addition, hosts were injected with an anti-CD154 mAb (day 0) and/or CTLA4Ig (day +2). Chimerism in peripheral blood was followed by FACS analysis, and tolerance was assessed by skin grafting, and also by MLR and CML assays. The frequency of certain Vβ families was determined by FACS to assess deletion of donor-reactive T cells.

Chimerism was transient and tolerance was not present in animals receiving TCD mAbs on day −5 without costimulatory blockade. The addition of anti-CD154 mAb (CD154 is also called CD40 ligand and gp39) and CTLA4Ig, alone or in combination, reliably permitted induction of high levels of stable (>6 months) multilineage chimerism, with specific tolerance to skin grafts and donor antigens by MLR and CML assays. Long-term chimeras showed deletion of donor-reactive $CD4^+$ PBL, splenocytes and mature thymocytes. Administration of TCD mAbs only one day prior to bone marrow transplantation (BMT) plus anti-CD 154 mAb also allowed induction of permanent chirmerism and tolerance.

Thus, one injection of anti-CD154 mAb or CTLA4Ig overcomes the need for TI or prolonged host TCD for the induction of mixed chimerism and deletional tolerance and thus further decreases the toxicity of this protocol. Achievement of tolerance with conditioning given over 24 hours makes this approach even more useful for cadaveric organ transplantation.

This example is discussed in more detail below.

Animals

The sources and treatment of animals was essentially the same as in Example 1.

Conditioning and Bone Marrow Transplantation (BMT)

Age-matched (6–13 weeks old) female B6 mice received 3 Gy WBI and were injected intravenously on the same day (d0) with unseparated bone marrow (BM) harvested from the femurs and tibiae of fully MHC-mismatched female B10.A donors (10–13 weeks old). The recipients were injected intraperitoneally (i.p.) with depleting doses of rat IgG2b anti-mouse CD4 mAb GK1.5 (approximately 1.8 mg per mouse) and anti-mouse CD8 mAb 2.43 (approximately 1.4 mg per mouse) on days −5 and −1 (Group A) or on day −5 alone (Groups B, C, D, E). On the day before BMT the success of T cell depletion was checked by FACS in PBL, and clear failures were excluded from further analysis. In the third experiment, GK1.5 and 2.43 were administered on day −1, approximately 24 hours before BMT. Murine CTLA4Ig was injected i.p. as a single dose (0.5 mg) on day +2, and hamster anti-mouse CD154 mAb (MR1) was injected i.p. on day 0 (0.45 mg). CTLA4Ig was a generous gift of Bristol-Myers, Squibb Pharmaceuticals, Seattle, Wash.; the MR1 hybridoma was kindly provided Dr. Randolph J. Noelle (Dartmouth Medical School, Lebanon, N.H.). A hamster anti-mouse IgG mAb (Cappel, ICN Pharmaceuticals, Aurora, Ohio) and the murine mAb L6 (Bristol-Myers, Squibb Pharmaceuticals, Seattle, Wash.) were injected as controls on day 0 and day +2 in the second experiment.

Flow Cytometric Analysis of Chimerism

Preparation of tissues: Approximately 0.4 ml. of peripheral blood were collected into heparinized tubes, and red blood cells were lysed with deionized water. Thymi and spleens were harvested from the animals and gently crushed with the base of a syringe. Spleens were crushed in ACK Lysing Buffer (Biowhittaker, Walkersville, Md.) to lyse red cells. Bone marrow cells were harvested from the femurs and tibiae by flushing the bones with medium. Cells were resuspended in FACS medium containing 1×HBSS, 0.1% sodium azide, and 0 1% bovine serum albumin (Fisher Scientific, Fair Lawn, N.J.).

Allogeneic reconstitution of various lineages in WBC, spleen, BM and thymus was evaluated by two-color FACS. Briefly, forward angle and 90 degree light scatter properties were used to distinguish lymphocytes, monocytes and granulocytes in peripheral WBC. Two-color FACS was utilized to distinguish donor and host cells of particular lineages, and the percentage of donor cells was calculated by subtracting control staining from quadrants containing donor and host cells expressing a particular lineage marker, and by dividing the net percentage of donor cells by the total net percentage of donor plus host cells of that lineage. Dead cells were excluded using propidium iodide staining. Non-specific FcγR binding was blocked by anti-mouse FcγR mAb 2.4G2. Fluorescein isothiocyanate (FITC)-conjugated mAbs included anti-CD4, anti-CD8, anti-B220 (all purchased from PharMingen, San Diego, Calif.) and anti-MAC1 (Caltag, San Francisco, Calif.). Negative control mAb HOPC1-FITC with no reactivity to mouse cells, was prepared in our laboratory. Biotinylated anti-H-2D$^d$ mAb 34-2-12 and control mAb HOPC1 were developed with phycoerythrin-streptavidin (PEA).

Flow Cytometric Analysis of T Cell Receptor Vβ Families

These methods were performed essentially as described in Example 1.

Mixed Lymphocyte Reactions (MLR)

Splenocytes were cultured in triplicate wells of 96-well flat-bottomed plates containing 4×10$^5$ responders with 4×10$^5$ stimulators (30 Gy irradiated, $^{137}$Cs source) in RPMI 1640 medium (Gibco, Grand Island, N.Y.) supplemented with 15% (vol/vol) controlled processed serum replacement (CPSR-2, Sigma), 4% nutrient mixture (7.3 mg/ml L-glutamine, 4×nonessential amino acids (Gibco), 2.75 mg/ml sodium pyruvate, 250 U/ml penicillin and 250 mg/ml streptomycin), 1% HEPES buffer, and 10 mM 2-mercaptoethanol at 37° C. in 5% CO$_2$ for 3 to 4 days before they were pulsed with [$^3$H] thymidine and harvested approximately 18 hours later. Stimulation indices were calculated by dividing mean counts per minute (CPM) from anti-donor and anti-third party responses by mean CPM from anti-host responses, which were similar to background CPM (i.e., CPM with no stimulator cell population).

Cell Mediated Lympholysis (CML) Assay

Splenocytes from controls, BMT recipients and normal mice were resuspended in RPMI 1640 (Mediatech, Herndon, Va.) containing 10% fetal bovine serum (Sigma, St. Louis, Mo.), 0.09 mM non-essential amino acids, 2 mM L-glutamine, 1 mM sodium pyruvate, 100 U/ml penicillin, and 0.2 μg/ml streptomycin, 0.025 mM 2-ME, and 0.01M HEPES buffer. Responder and stimulator cells (30 Gy irradiated, $^{137}$Cs source) were diluted to a concentration of 8×10$^6$ cells/ml. 8×10$^5$ responder cells were co-cultured with 8×10$^5$ stimulator cells per well in 96-well round bottom plates. Cultures were set up in two rows of three replicates each, and after five days of incubation in 8% CO$_2$ at 37° C., two-fold serial dilutions were prepared from the second row of triplicates, so that cytolytic capacity could be examined at five different responder to target ratios. 8×10$^{3 \; 5 \; 51}$Cr-labeled, two-day concanavalin-A-stimulated lymphoblasts were added to each well and incubated for four hours in 8% CO$_2$ at 37° C. Plates were harvested by using the Titertek supernatant collection system (Skatron, Inc., Sterling, Va.) and $^{51}$Cr release was determined with an automated gamma counter. Percent specific lysis was calculated with the formula:

% Specific Lysis=[(experimental release−spontaneous release)/ (maximum release−spontaneous release)]×100%.

Immunohistochemical Staining

Frozen thymus sections (4 μm) were prepared and stained as previously described (21). Briefly, sections were stained with ISCR-3 (mouse IgG2b-anti-MHC class II I-E, 1:200 dilution of ascites) and 25-9-17 (mouse IgG2a-anti-MHC class II I-A$^b$, 1:50 dilution). Ascites containing HOPC-1 mAb (non-reactive mouse IgG2a, 1:100 dilution) or 74-11-10 (mouse IgG2b-anti-pig MHC class I, 1:200 dilution) were used as negative control stains. Biotinylated rat anti-mouse IgG2a or IgG2b mAbs were used as secondary reagents. Staining was developed using the Vectastain ABC kit (Vector Corporation, Burlingame, Calif.).

Skin Grafting

Full thickness tall skin from B10. A (donor-specific) and fully MHC-mismatched A.SW (third party) mice was -rafted onto the lateral thoracic wall 5 to 10 weeks after BMT, secured with 5–10 silk sutures and bandaids which were removed one week later. Grafts were then followed by daily visual and tactile inspections for the first three weeks, and at least weekly thereafter. Grafts were defined as rejected when less than 10% of the graft remained viable.

Statistical Analysis

Statistical significance was determined with a two-tailed Student's T test for comparison of means with unequal variances. Differences between groups were considered to be significant if p<0.05.

Multilineage Hematopoietic Chimerism in WBC

All mice in the described experiments received a non-myeloablative dose of 3 Gy WBI and $15\times10^6$ BMC (with the exception of control mice receiving conditioning without BM), with TCD antibodies and costimulatory blocking antibodies added to this conditioning as indicated. Donor hematopoiesis in WBC was assessed at multiple time-points after BMT. The net percentage of donor cells in different lineages was determined by staining with a mAb specific for donor class-I versus various lineage markers.

One group of recipients (Group A) was treated with the previously described regimen (Tomita et al., 1996, Transplantation 61: 469.) of two doses of TCD mAbs on days −5 and −1. Three of five of these recipients developed long-lasting multilineage chimerism, with the mean percentage of donor representation among CD4 and CD8 cells being lower than donor chimerism among B cells and myeloid lineages. The remaining two mice initially developed high levels of B cell and myeloid chimerism, but lower levels of T cell chimerism (apparent at 7 weeks), and chimerism in all lineages began to decline soon after BMT.

Another control group of mice received only one dose of TCD mAb on day −5 without further treatment (Group B). This conditioning led to high levels of initial donor reconstitution among B cells and myeloid cells, but failed to lead to substantial levels among T cells beyond week seven. Four out of five mice thereafter demonstrated a sharp decline in their chimerism levels.

To study whether CTLA4Ig and anti-CD154 mAb could allow induction of lasting chimerism and tolerance without a second dose of TCD mAbs (or thymic irradiation), they were added to the conditioning regimen of TCD mAbs administered only on day −5. CTLA4Ig given alone in a single dose on day +2 (Group C), led to high levels of donor repopulation in all lineages in three out of five mice.

When a single dose of anti-CD154 mAb was administered on day 0 (Group D), high levels of stable donor chimerism in all lineages were induced in all five recipients. Seven weeks after BMT, the percentage of donor cells was higher than 50% among T cells, B cells, monocytes and granulocytes in all animals and remained stable for more than 6 months, demonstrating the engraftment of pluripotent stem cells.

The treatment of recipients with a combination of anti-CD154 mAb (day 0) plus CTLA4Ig (day +2) (Group E), resulted in similar chimerism levels as those observed with anti-CD154 mAb alone. All six mice developed high levels of stable multilineage chimerism. that were similar to those in Group D, with no clear advantage of this combination treatment over the administration of anti-CD154 mAb alone.

In the group of mice conditioned with TCD on day −5 plus a control hamster mAb and a control murine mAb, chimerism followed a course comparable to Group B, with high initial levels among B cells and myeloid cells that soon began to decline.

The mean level of donor representation in WBC observed in mice receiving costimulatory blockade (Groups C, D and E) was not only higher than in Group B, but was also higher than in mice receiving two doses of TCD mAbs (Group A). Especially noteworthy was the high level of donor T cell chimerism, which is a predictor of tolerance development in the non-myeloablative model. In several mice T cell chimerism was higher than mycloid chimerism, an opposite pattern to that seen in mice conditioned with two doses of TCD mAbs. These results were confirmed in a second, separate experiment, which gave a comparable outcome, with increased multilineage chimerism in recipients of CTLA4Ig and/or anti-CD154 mAb compared to the control group receiving TCD mAbs on day −5 and −1.

These results indicate that CTLA4Ig and anti-CD154 mAb as single agents are each effective at obviating the need for prolonged TCD or TI in this model, leading to high levels of stable chimerism among all tested hematopoietic lineages.

One-day Conditioning Regimen

Since the conditioning regimen described above begins five days before BMT, it would not be optimum for use with cadaveric organ donors. The conditioning was modified by administering the TCD mAbs only approximately 24 hours before the BMT in a third experiment (n=3). Anti-CD154 mAb was chosen for use in this protocol. High levels of multilineage chimerism were achieved after conditioning with TCD mAbs on day −1 and anti-CD154 mAb on day 0 without any apparent loss of efficacy, further increasing the clinical usefulness of this approach.

Hematopoietic Chimerism in Spleen, Thymus and BM

At the time of sacrifice (29 weeks post-BMT), chimerism in spleen, thymus and bone marrow was determined by FACS in a subgroup of mice to confirm the presence of multilineage chimerism and thus stem cell engraftment. As shown in Table 1, similarly high levels of donor representation were observed among $CD4^+$, $CD8^+$ and $B220^+$ splenocytes, among mature thymocytes and among bone marrow cells, in all three groups receiving costimulatory blockade. No statistically significant difference between these three groups was seen for any tissue or lineage. Comparable results were seen 43 weeks post-BMT in the second experiment, confirming that substantial engraftment of donor stem cells had occurred.

The percentage of donor cells among $CD4^+$, $CD8^+$, $B220^+$ splenocytes, thymocytes and bone marrow cells was determined by FACS at the time of sacrifice 29 weeks post BMT. Results from one of two similar experiments are shown as mean percentage of donor representation. Group A (n=1): TCD day −5, day −1; group B (n=1): TCD day −5 only; group C (n=2): TCD day −5 plus CTLA4Ig; group D (n=2): TCD day -5 plus anti-CD154 mAb; group E (n=2): TCD day −5 plus CTLA4Ig plus anti-CD154 mAb. P-value is non-significant for comparison between groups C, D and E. NL B6 and NL B10.A denote normal B6 and normal B10.A, respectively.

Skin Graft Survival

To determine whether donor-specific tolerance was induced, skin grafting, which is the most stringent test for transplantation tolerance, was performed. Donor and third-party skin was grafted ten weeks, seven weeks (second experiment) or five weeks (third experiment) after BMT. In the group receiving two doses of TCD mAbs (Group A) the three successful chimeras accepted donor skin grafts permanently (>130 days), while all mice prepared with TCD mAbs only on day −5 without further treatment (Group B)

rejected their grafts within 15 days, consistent with the absence of long-term chimerism.

In the group of recipients treated with TCD mAbs on day −5 plus CTLA4Ig alone (Group C), donor grafts were accepted permanently by the three successful chimeras. One of the two mice that failed to develop high levels of multilineage chimerism. rejected its donor graft on day 9, and the second one died with its graft still in good condition 16 days after BMT. All animals receiving anti-CD154 mAb alone (Group D) or anti-CD154 mAb plus CTLA4Ig (Group E) accepted their donor grafts permanently. Long-term surviving grafts remained in perfect condition with a follow-up of up to 160 days.

Control mice receiving conditioning without BMT, or TCD mAbs on day −5 plus control antibodies, promptly rejected their donor grafts. All groups uniformly rejected third party grafts within two weeks, indicating that the induced tolerance was specific and that the chimeras were immunocompetent.

The second experiment showed similar donor-specific skin graft acceptance in mice receiving TCD and costimulatory blockade. The chimeras in the third experiment receiving TCD mAbs on day −1 and anti-CD154 mAb accepted their donor grafts (>40 days), while rejecting third party grafts promptly.

MLR and CML Reactivity

To further evaluate the development of tolerance, MLR and CML assays were performed at the time of sacrifice in the first experiment. Four out of six tested chimeras from Groups C, D and E showed unresponsiveness toward donor antigens, while maintaining reactivity to third-party antigens (stimulation index >1.9). The chimera from Group A, one of two chimeras each from Groups C and E, the mouse from Group B, and a control receiving the conditioning without BMT, were globally hyporesponsive. Results from the CML assays showed a similar pattern as seen with MLR reactivity (Table 2). One chimera from each of Groups C and D demonstrated effective killing of third-party targets while not killing donor targets. The remaining animals, including the control mouse that did not receive BMT, showed general hyporesponsiveness, even though immunocompetence was demonstrated in vivo by the ability to promptly reject third party skin grafts. Although the senescence of the mice may have caused the generalized in vitro hyporesponsiveness observed in some cases, these MLR and CML studies overall provide further evidence for the presence of donor-specific tolerance in chimeras prepared with costimulatory blockade.

Deletion of Donor-reactive T Cells

Central deletion is the main mechanism for the maintenance of tolerance in the mixed chimerism model. Deletion of donor-reactive T cells in PBL, thymus and spleen was examined by analyzing the occurrence of certain $V\beta$ subunits on the TCR. The donor strain B10.A expresses I-E, which is required to present superantigens derived from the Mammary tumor virus (Mtv)-8 and -9 endogenous retrovirnses encoded in the B6/B10 background genome. Developing thymocytes, whose TCR contain $V\beta 11$ or $V\beta 5\frac{1}{2}$, which bind to these superantigens, are deleted in I-E-positive B10.A mice, but not in B6 mice, because they do not express I-E. At 8 weeks post-BMT (in the first experiment), all mice in Groups A, D and E and 4 out of 5 mice in Group C (one of the mice that had declining levels of chimerism showed incomplete deletion) demonstrated a profound reduction in $V\beta 5^+$ and $V\beta 11^+$ $CD4^+$ PBL, but no decline in $V\beta 8^+$ control $CD4^+$ PBL. The deletion in Groups D and E was significantly more pronounced than in Group B, consistent with the gradual loss of chimerism and tolerance in the latter group. At the time of sacrifice 43 weeks post-BMT (second experiment), all tested animals in Groups C, D and E showed a profound reduction in the percentage of $V\beta 5^+$ mature host-type thymocytes compared to a naive B6 mouse or a control receiving the conditioning without BMT. At the same time point, the percentages of $V\beta 5$ and $V\beta 11$ positive recipient $CD4^+$ and $CD8^+$ splenocytes were also drastically reduced. Taken together, these data suggest that central deletion of donor-reactive T cells is the major mechanism of tolerance in long-term chimeras prepared with this regimen.

Donor Class II$^+$ Cells in Thymus

Cells of hematopoictic origin are important mediators of negative selection in the thymus with dendritic cells being among the most potent subpopulations in this respect. We therefore looked for donor cells with dendritic cell morphology in thymi of chimeras at the time of sacrifice (29 weeks post-BMT). All chimeras tested (two each from Groups C, D, and E) showed the presence of donor class II$^+$ cells with dendritic cell morphology. A control mouse receiving the conditioning without BMT was negative for donor class II$^+$ cells. Host class II$^+$ cells were distributed normally in all recipients. These findings support the conclusion that intrathymic deletion is a major mechanism of tolerance during long-term follow-up.

The present studies demonstrate that T cell costimulatoiy blockade is a potent. Both anti-CD 154 mAb and CTLA4Ig were effective as single agents in replacing thymic irradiation or the repeated administration of TCD mAbs. The clinical relevance of this newly developed regimen for tolerance induction is further increased by the ability to begin the conditioning treatment only 24 hours before BMT, making it applicable to cadaveric organ transplantation.

TABLE 1

Chimerism in spleen, thymus and bone marrow

| | Mean Percentage of Donor Cells | | | | |
|---|---|---|---|---|---|
| | Spleen | | | | |
| | CD4$^+$ | CD8$^+$ | B cells | Thymus | Bone Marrow |
| NL B10.A | 98.94 | 99.64 | 100.00 | 29.85 | 64.09 |
| NL B6 | 0.41 | 1.61 | 0.53 | 0.04 | 0.08 |
| group A | 11.21 | 24.41 | 64.86 | 38.38 | 28.79 |
| group B | 0.42 | 0.00 | 1.15 | 0.04 | 1.86 |
| group C | 67.86 | 72.33 | 79.83 | 10.15 | 46.59 |
| group D | 76.53 | 80.05 | 88.69 | 19.60 | 50.97 |
| group E | 74.72 | 67.08 | 75.54 | 25.49 | 62.34 |

The percentage of donor cells among CD4$^+$, CD8$^+$, B220$^+$ splenocytes, thymocytes and bone marrow cells was determined by FACS at the time of sacrifice 29 weeks post BMT. Results from one of two similar experiments are shown as mean percentage of donor representation. Group A (n=1): TCD day −5, day −1; group B (n=1): TCD day −5 only; group C (n=2): TCD day −5 plus CTLA4Ig; group D (n=2): TCD day −5 plus anti-CD154 mAb; group E (n=2): TCD day −5 plus CTLA4Ig plus anti-CD154 mAb. P-value is non-significant for comparison between groups C, D and E. NL B6 and NL B10.A denote normal B6 and normal B10.A, respectively.

TABLE 2

CML assays

Percent Specific Lysis

|  | anti-self (B6) | anti-donor (B10.A) | anti-3rd party (A.SW) |
|---|---|---|---|
| NL B6 | 0.17 | 29.17 | 91.43 |
| no BMT | −3.78 | 7.44 | 6.85 |
| group A | −1.05 | 4.34 | 7.94 |
| group B | −0.43 | 6.92 | 7.40 |
| group C | −2.87 | 2.04 | 2.22 |
|  | −2.36 | −1.06 | 51.66 |
| group D | −5.45 | 0.16 | −2.72 |
|  | −5.12 | −2.03 | 46.44 |
| group E | −1.31 | 7.59 | −1.53 |
|  | −2.99 | 2.58 | 10.78 |

Results from CML assays are shown as percent specific lysis against self (B6), third party (A.SW) and donor (B10.A) targets, 29 weeks post-BMT (first experiment). The highest responder: target ratio tested (100:1) is presented. NL B6 and NL B10.A denote normal B6 and normal B10.A, respectively. No BMT denotes a mouse receiving conditioning (WBI, TCD mAbs day −5, CTLA4Ig plus anti-CD154 mAb) without BMT. For group descriptions see Table 1.

Other Embodiments

The methods described herein for inducing tolerance to, or promoting the acceptance of, an allogeneic antigen or allogeneic graft can be used where, as between the donor and recipient, there is any degree of mismatch at MHC loci or other loci which influence graft rejection. There can be a mismatch at at least one MHC locus or at at least one other locus that mediates recognition and rejection, e.g., a minor antigen locus. With respect to class I and class II MHC loci, the donor and recipient can be: matched at class I and mismatched at class II; mismatched at class I and matched at class II; mismatched at class I and mismatched at class II; matched at class I, matched at class II. In any of these combinations other loci which control recognition and rejection, e.g., minor antigen loci, can be matched or mismatched. As stated above, it is preferable that there is mismatch at least one locus. Mismatched at MHC class I means mismatched for one or more MHC class I loci, e.g., in the case of humans, mismatched at one or more of HLA-A, HLA-B, or HLA-C. Mismatched at MHC class II means mismatched at one or more MHC class II loci, e.g., in the case of humans, mismatched at one or more of a DPα, a DPβ, a DQα, a DQβ, a DRα, or a DR.

The methods described herein for inducing tolerance to an allogeneic antigen or allogencic graft can be used where, as between the donor and recipient, there is any degree of reactivity in a mixed lymphocyte assay, e.g., wherein there is no, low, intermediate, or high mixed lymphocyte reactivity between the donor and the recipient. In preferred embodiments mixed lymphocyte reactivity is used to define mismatch for class II, and the invention includes methods for performing allogeneic grafts between individuals with any degree of mismatch at class II as defined by a mixed lymphocyte assay. Serological tests can be used to determine mismatch at class I or II loci and the invention includes methods for performing allogeneic grafts between individuals with any degree of mismatch at class I and or II as measured with serological methods. In a preferred embodiment, the invention features methods for performing allogeneic grafts between individuals which, as determined by serological and or mixed lymphocyte reactivity assay, are mismatched at both class I and class II.

The methods of the invention are particularly useful for replacing a tissue or organ afflicted with a neoplastic disorder, particularly a disorder which is resistant to normal modes of therapy, e.g., chemotherapy or radiation therapy. Methods of the invention can be used for inducing tolerance to an allograft, e.g., an allograft from a donor which is mismatched at one or more class I loci, at one or more class II loci, or at one or more loci at each of class I and class II. In preferred embodiments: the graft includes tissue from the digestive tract or gut, e.g., tissue from the stomach, or bowel tissue, e.g., small intestine, large intestine, or colon; the graft replaces a portion of the recipient's digestive system e.g., all or part of any of the digestive tract or gut, e.g., the stomach, bowel, e.g., small intestine, large intestine, or colon.

It is possible to induce mixed chimerism with less radiation toxicity by fractionating the radiation dose, i.e., by delivering the radiation in two or more exposures or sessions. Accordingly, in any method of the invention calling for the irradiation of a recipient, e.g., a primate, e.g., a human, recipient, of an allograft, the radiation can either be delivered in a single exposure, or more preferably, can be fractionated into two or more exposures or sessions. The sum of the fractionated dosages is preferably equal, e.g., in rads or Gy, to the radiation dosage which can result in mixed chimerism when given in a single exposure. The fractions are preferably approximately equal in dosage. Hyperfractionation of the radiation dose can also be used in methods of the invention. The fractions can be delivered on the same day, or can be separated by intervals of one, two, three, four, five, or more days. Whole body irradiation, thymic irradiation, or both, can be fractionated.

Thymic irradiation can also be fractionated. For example, a single dose of 700 cGy can be replaced with, e.g., two fractions of 350 cGy, or seven fractions of 100 cGy.

Methods of the invention can include recipient splenectomy.

In any of the methods described herein, particularly primate or clinical methods, it is preferable to form mixed chimerism as opposed to entirely replacing the recipient's stem cells with donor cells.

Blockers of the CD40 ligand-CD40 interaction (and optionally the CD28-B7 interaction) (or both) can be administered repeatedly. E.g., blockers can be administered one, two, three, or more times prior to donor bone marrow transplantation. Typically, a pre-bone marrow transplantation dose will be given to the patient at about 0 and −2 days. Additional, earlier doses 6, 7, or 8 days prior to bone marrow transplantation can also be given. It may be desirable to administer a first treatment then to repeat pre-bone marrow administration every 1–5 days. Blockers can also be administered one, two, three, or more times after donor bone marrow transplantation. Typically, a post-bone marrow transplant treatment will be given about 2–14 days after bone marrow transplantation. The post bone marrow administration can be repeated as many times as needed. If more than one administration is given the administrations can be spaced about 1 week apart. Additional doses can be given if the patient appears to undergo early or unwanted T cell recovery. Preferably, blockers are administered at least once (and preferably two, three, or more times) prior to donor bone marrow transplantation and at least once (and preferably two, three, or more times) after donor bone marrow transplantation.

CD40–CD40L blockers can be administered prior to CD28-B7 blockers, if CD2-B7 blockers are used. They can also be administered at the same time or after CD2-B7 blockers, if CD2-B7 blockers are used.

Some of the methods herein include the administration of hematopoietic stem cells to a recipient. In many of those methods, hematopoietic stem cells are administered prior to or at the time of the implantation of a graft, the primary purpose of the administration of hematopoictic stem cells being the induction of tolerance to the graft. The inventors have found that one or more subsequent administration (e.g., a second, third, fourth, fifth, or further subsequent administration) of hematopoictic stem cells can be desirable in the creation and/or maintenance of tolerance. Thus, the invention also includes methods in which hematopoietic stem cells are administered to a recipient, e.g., a primate, e.g., a human, which has previously been administered hematopoietic stem cells as part of any of the methods referred to herein.

While not wishing to be bound by theory the inventor believes that repeated stem cell administration may promote mixed chimerism and possibly long-term deletional tolerance in graft recipients. Accordingly, any method referred to herein which includes the administration of hematopoletic stem cells can further include multiple administration of stem cells. In preferred embodiments: a first and a second administration of stem cells are provided prior to the implantation of a graft; a first administration of stem cells is provided prior to the implantation of a graft and a second administration of stem cells is provided at the time of implantation of the graft. In other preferred embodiments: a first administration of stem cells is provided prior to or at the time of implantation of a graft and a second administration of stem cells is provided subsequent to the implantation of a graft. The period between administrations of hematopoietic stem cells can be varied. In preferred embodiments a subsequent administration of hematopoietic stem cell is provided: at least two days, one week, one month, or six months after the previous administration of stem cells; at least two days, one week, one month, or six months after the implantation of the graft.

The method can further include the step of administering a second or subsequent dose of hematopoietic stem cells: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft. Thus, method of the invention can be modified to include a further step of determining if a subject which has received a one or more administrations of hematopoietic stem cells is in need of a subsequent administration of hematopoietic stem cells, and if so, administering a subsequent dose of hematopoietic stem cells to the recipient.

Any of the methods referred to herein can include the administration of agents, e.g., 15-deoxyspergualin, mycophenolate mofetil, brequinar sodium, or similar agents, which inhibit the production, levels, or activity of antibodies in the recipient. One or more of these agents can be administered: prior to the implantation of donor tissue, e.g., one, two, or three days, or one, two, or three weeks before implantation of donor tissue; at the time of implantation of donor tissue; or after implantation of donor tissue, e.g., one, two, or three days, or one, two or three weeks after, implantation of a graft.

The administration of the agent can be initiated: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft.

The period over which the agent is administered (or the period over which clinically effective levels are maintained in the subject) can be long term, e.g., for six months or more or a year or more, or short term, e.g., for less than a year, more preferably six months or less, more preferably one month or less, and more preferably two weeks or less. The period will generally be at least about one week and preferably at least about two weeks in duration. In preferred embodiments the period is two or three weeks long.

Preferred embodiments include administration of 15-deoxyspergualin (6 mg/kg/day) for about two weeks beginning on the day of graft implantation.

An anti-CD2 antibody, preferably a monoclonal, e.g., BTI-322, or MEDI-507,or a monoclonal directed at a similar or overlapping epitope, can be used in addition to or in place of any anti-T cell antibodies (e.g., ATG) in any method referred to herein. BTI-322 is a rat monoclonal anti-CD2 antibody. MEDI-507 is a humanized version of BTI-322. BTI-322 is described in U.S. Pat. No. 5,817,311, hereby incorporated by reference. BTI-322 has been deposited with the ATCC as accession number HB 11423. MEDI-507 is described in PCT/US97/12645 (WO9903502, published Jan. 28, 1999), hereby incorporated by reference.

Other embodiments are within the following claims.

What is claimed is:

1. A method of promoting acceptance, by a recipient mammal, of a graft from a donor mammal of the same species comprising:
administering to the recipient, an inhibitor of the CD40 ligand-CD40 costimulatory interaction;
introducing into the recipient mammal, hematopoietic stem cells, and
implanting the graft in the recipient.

2. The method of claim 1, further comprising administering an inhibitor of the CD28-B7 interaction.

3. The method of claim 1, wherein the CD40 ligand-CD40 interaction is inhibited by administering an antibody or soluble ligand or receptor for the CD40 ligand or CD40.

4. The method of claim 1, wherein an anti-CD40L antibody is administered.

5. The method of claim 2, wherein the CD28-B7 interaction is inhibited by administering a soluble ligand or receptor or antibody for the CD28 or B7.

6. The method of claim 5, wherein CTLA4/Ig is administered.

7. The method of claim 2, wherein CTLA4-Ig and an anti-CD40L antibody are administered.

8. The method of claim 2, wherein a blocker of the CD40/CD40L interaction is administered prior to administration of a blocker of the CD28/B7 interaction.

9. The method of claim 1, wherein the recipient mammal is a human.

10. The method of claim 1, wherein the method is practiced without thymic irradiation or anti-T cell antibodies.

11. The method of claim 1, wherein the method is practiced without T cell depletion or inactivation.

12. The method of claim 1, wherein the method is practiced with T cell depletion or inactivation.

13. The method of claim 1, wherein the method is practiced with partial T cell depletion or inactivation.

* * * * *

UNITED STATES PATENT AND TRADEMARK OFFICE
CERTIFICATE OF CORRECTION

PATENT NO. : 6,280,957 B1
DATED : August 28, 2001
INVENTOR(S) : Sayegh et al.

It is certified that error appears in the above-identified patent and that said Letters Patent is hereby corrected as shown below:

<u>Title page,</u>
Item [73], should read as follows:
-- (73) Assignee: The General Hospital Corporation,
Charlestown, MA (US)

Brigham & Women's Hospital,
Boston, MA (US) --

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,280,957 B1
DATED : August 28, 2001
INVENTOR(S) : Megan Sykes and Mohamed H. Sayegh It is certified that error appears in the above-identified patent and that said Letters Patent is hereby corrected as shown below:

Column 1,
Line 3, insert the following:

-- FEDERALLY SPONSORED RESEARCH OR DEVELOPMENT

This invention was made with Government support under Contract #NIH HL49915 awarded by the National Institutes of Health. The Government has certain rights in this invention. --

Signed and Sealed this

Thirteenth Day of April, 2004

JON W. DUDAS
*Acting Director of the United States Patent and Trademark Office*